US011660550B2

(12) United States Patent
Van Alstine

(10) Patent No.: US 11,660,550 B2
(45) Date of Patent: May 30, 2023

(54) MODIFIED ADSORPTIVE SURFACES

(71) Applicant: JMVA BIOTECH AB, Stockholm (SE)

(72) Inventor: James M. Van Alstine, Stockholm (SE)

(73) Assignee: JMVA BIOTECH AB, Stockholm (SE)

( * ) Notice: Subject to any disclaimer, the term of this patent is extended or adjusted under 35 U.S.C. 154(b) by 0 days.

(21) Appl. No.: 16/490,912

(22) PCT Filed: Mar. 6, 2018

(86) PCT No.: PCT/EP2018/055506
§ 371 (c)(1),
(2) Date: Sep. 4, 2019

(87) PCT Pub. No.: WO2018/162501
PCT Pub. Date: Sep. 13, 2018

(65) Prior Publication Data
US 2019/0388804 A1     Dec. 26, 2019

Related U.S. Application Data
(60) Provisional application No. 62/468,034, filed on Mar. 7, 2017.

(51) Int. Cl.
| | | |
|---|---|---|
| *B01D 15/38* | (2006.01) | |
| *B01J 20/286* | (2006.01) | |
| *B01J 20/32* | (2006.01) | |
| *C07K 1/22* | (2006.01) | |
| *B01J 20/289* | (2006.01) | |
| *B01J 20/288* | (2006.01) | |

(52) U.S. Cl.
CPC ........ *B01D 15/3809* (2013.01); *B01J 20/286* (2013.01); *B01J 20/288* (2013.01); *B01J 20/289* (2013.01); *B01J 20/3219* (2013.01); *B01J 20/3274* (2013.01); *C07K 1/22* (2013.01)

(58) Field of Classification Search
CPC .. B01J 20/28016; B01J 20/286; B01J 20/289; B01J 20/288; B01J 20/281; B01J 20/3231; B01J 20/3242; B01J 20/328; B01J 20/3272; B01J 20/3274; B01J 20/3285; B01J 20/3202; B01J 20/3219; B01J 20/3221; B01J 20/3268; B01J 20/3217; B01J 20/3214; B01D 15/3804; B01D 15/3819; B01D 15/3809; B01D 15/3828; B01D 15/38; B01D 15/26
See application file for complete search history.

(56) References Cited

U.S. PATENT DOCUMENTS

| | | | | |
|---|---|---|---|---|
| 5,171,837 A | * | 12/1992 | Tanihara | ............ C07K 14/7155 530/324 |
| 6,686,457 B1 | * | 2/2004 | Nilsson | .................. B01D 15/00 536/4.1 |
| 6,831,161 B1 | | 12/2004 | Uhlen et al. | |
| 9,890,191 B2 | | 2/2018 | Minakuchi | |
| 9,896,486 B2 | * | 2/2018 | Rodrigo | .................... C07K 1/22 |
| 2002/0146814 A1 | * | 10/2002 | Nilsson | ................. B01J 20/3251 435/287.1 |
| 2006/0063276 A1 | * | 3/2006 | Jiang | .................... B01J 20/3212 436/518 |
| 2010/0221844 A1 | | 9/2010 | Bian et al. | |
| 2014/0178439 A1 | * | 6/2014 | Hjerten | .................. A61K 45/06 424/278.1 |
| 2016/0168229 A1 | | 6/2016 | Paolantonacci et al. | |
| 2017/0327534 A1 | * | 11/2017 | Rodrigo | ................. B01J 20/286 |
| 2017/0334954 A1 | * | 11/2017 | Rodrigo | ............... B01J 20/3274 |
| 2019/0375785 A1 | * | 12/2019 | Zong | .................... B01J 20/3212 |

FOREIGN PATENT DOCUMENTS

| | | |
|---|---|---|
| WO | 98/08603 A1 | 3/1998 |
| WO | 2013/117707 A1 | 8/2013 |
| WO | 2015/005859 A1 | 1/2015 |
| WO | 2016/079033 A1 | 5/2016 |
| WO | 2017/194596 A1 | 11/2017 |

OTHER PUBLICATIONS

Who, Iarc TP53 Database, "Amino acid properties," available at <https://p53.iarc.fr/AAproperties.aspx>, accessed Mar. 26, 2021, 2 pages. (Year: 2021).*
Braisted et al. "Minimizing a binding domain from protein A" (Pnas, vol. 93, Jun. 1996, p. 5688-5692). (Year: 1996).*
Rodrigo, Gustav et al., Antibody Fragments and Their Purification by Protein L Affinity Chromatography, Antibodies, vol. 4, No. 3, pp. 259-277 (2015).
Ljungquist, Charlotta et al., Thiol-directed immobilization of recombinant IgG-binding receptors, Eur. J. Biochem, vol. 186, pp. 557-561 (1989).
Pabst, Timothy M. et al., Engineering of novel Staphylococcal Protein A ligands to enable milder elution pH and high dynamic binding capacity, Journal of Chromatography A, vol. 1362, pp. 180-185 (2014).

(Continued)

*Primary Examiner* — Ryan B Huang
(74) *Attorney, Agent, or Firm* — Porter Wright Morris & Arthur LLP

(57) ABSTRACT

There is disclosed a relatively simple method to increase the performance of surface localised multi-valent affinity ligands whose target's isoelectric pH differs significantly from the ligand's optimal target-binding pH. This situation can result in ligand binding of target affecting local pH and subsequent binding of more target. Increasing the buffering capacity of the ligand via recombinant or other addition of charge groups to the ligand is expected to partially offset such effects, leading to enhanced binding capacity as well as possible secondary favourable alterations in regard to ligand elution pH, and non-specific surface binding of non-target proteins.

47 Claims, 16 Drawing Sheets
Specification includes a Sequence Listing.

(56) References Cited

OTHER PUBLICATIONS

Hober Sophia et al., Protein A chromatography for antibody purification, J. Chromatogr. B, vol. 848, Issue 1, pp. 40-47 (Mar. 15, 2007).

Ghose Sanchayita et al., Binding capacity differences for antibodies and Fc-fusion proteins on protein A chromatographic materials, Biotechnology and Bioengineering, vol. 96, Issue 4, pp. 768-779 (Mar. 1, 2007).

Levy, Nicholas E. et al., Identification and Characterization of Host Cell Protein Product-Associated Impurities in Monoclonal Antibody Bioprocessing, Biotechnology and Bioengineering, vol. 111, Issue 5, pp. 904-912 (May 2014).

Harinarayan, C. et al., An exclusion mechanism in ion exchange chromatography, Biotechnology and Bioengineering, vol. 95, Issue 5, pp. 775-787 (Dec. 5, 2006).

Gräslund, Torbjorn et al., Charge engineering of a protein domain to allow efficient ion-exchange recovery, Protein Engineering, vol. 13, Issue 10, pp. 703-709 (2000).

Yu, Feifan et al., Tailor-Making a Protein A—Derived Domain for Efficient Site-Specific Photocoupling to Fc of Mouse IgG1, Plos One, vol. 8, Issue 2, pp. 1-11 (Feb. 2013).

Karow, Anne R. et al., Buffer capacity of biologics—from buffer salts to buffering by antibodies, Biotechnology Progress, vol. 29, Issue 2, pp. 480-492 (Mar./Apr. 2013).

Zheng, Ziwei et al., Analytical methods for kinetic studies of biological interactions: A review, Journal of Pharmaceutical and Biomedical Analysis, vol. 113, pp. 163-180 (Sep. 10, 2015).

Becker, Kristian et al., Multipurpose peptide tags for protein isolation, Journal of Chromotography A, vol. 1202, Issue 1, pp. 40-46 (Aug. 15, 2008).

Åkerström, Bo et al., A Physicochemical Study of Protein G, a Molecule with Unique Immunoglobulin G-binding Properties, The Journal of Biological Chemistry, vol. 261, No. 22, pp. 10240-10247 (Aug. 5, 1986).

Braisted, Andrew C. et al., Minimizing a binding domain from protein A, Proc. Natl. Acad. Sci. USA, vol. 93, pp. 5688-5692, (Jun. 1996).

Silva, Goncalo L. et al., The pearl necklace model in protein A chromatography: Molecular mechanisms at the resin interface, Biotechnology and Bioengineering, vol. 116, pp. 76-86 (2019).

Weinberg, Justin et al., Polyclonal and Monoclonal IgG Binding on Protein A Resins—Evidence of Competitive Binding Effects, Biotechnology and Bioengineering, vol. 114, pp. 1803-1812 (2017).

Winzor, Donald J., Determination of binding constants by affinity chromatography, Journal of Chromotography A, vol. 1037, pp. 351-367 (2004).

Ecker, Dawn M. et al., The therapeutic monoclonal antibody market, BioProcess Technology Consultants, Inc., vol. 7, No. 1, pp. 9-14 (Jan./Feb. 2015).

Tran Richard, et al., A Methodology for the Comparative Evaluation of Alternative Bioseparation Technologies, Biotechnol. Prog., vol. 24, pp. 1007-1025 (2008).

Strauch, Eva-Maria, Computational design of a pH-sensitive IgG binding protein, PNAS, vol. 111, No. 2, pp. 675-680 (Jan. 14, 2014).

Choe, W. et al., Fc-Binding Ligands of Immunoglobulin G: An Overview of High Affinity Proteins and Peptides, Materials, vol. 9, No. 994, pp. 1-17 (2016).

Sakhnini, Laila I. et al., Improving the Developability of an Antigen Binding Fragment by Aspartate Substitutions, Biochemistry, vol. 58, pp. 2750-2759 (2019).

Zhang, S. et al., Nature of foulants and fouling mechanism in the Protein A MabSelect resin cycled in a monoclonal antibody purification process, Biotechnol. Bioeng., vol. 113, pp. 141-149 (2016).

Roque, C.A. et al., Antibodies and genetically engineered related molecules: Production and purification, Biotechnol. Prog., vol. 20, pp. 639-654 (2004).

Malmsten M. et al., Adsorption of Complement Proteins C3 and C1q, J. Colloid Interf. Sci., vol. 178, pp. 123-134 (1996).

Minakuchi, Kazunobu et al., Remarkable alkaline stability of an engineered protein A as immunoglobulin affinity ligand: C domain having only one amino acid substitution, Protein Science, vol. 22, pp. 1230-1238 (2013).

https://en.wikipedia.org/wiki/Alpha_helix, dated Dec. 8, 2021.

Pace et al., "A Helix Propensity Scale Based on Experimental Studies of Peptides and Proteins", Biophysical Journal, 75:422-427 (1998).

* cited by examiner

Schematic of Tetrameric Z Domain Antibody Binding Ligands – Unmodified, Neutral Residue Enhanced, and Charge Residue Enhanced - Between Z domains

a. "Native" Control ligand based on four Z domains.

b. Experimental ligand based on four Z domains with three negatively charged aspartate (D) residues added to the Z joining (AJR) regions and a terminal region.

c. Control ligand based on four Z domains with neutral glycine (G) or serine (S) residues added to the Z joining (AJR) regions and a terminal region.

Fig. 5

Net charge based on amino acid sequence as a function of pH for Mab1 (●), Mab2 (▲) and Mab3 (◆).

For some mAbs the -20 charge offset may allow 3 mAbs to bind to each ligand
Genentech mAb data from Biotech and Bioeng, 95: 775-787, 2006

1)4_Z_GGS

MGSSHHHHHH SSGLVPRGSH MVDNKFNKEQ QNAFYEILHL PNLNEEQRNA FIQSLKDDPS
QSANLLAEAK KLNDAQAPKG SSVDNKFNKE QQNAFYEILH LPNLNEEQRN AFIQSLKDDP
SQSANLLAEA KKLNDAQAPK SGGVDNKFNK EQQNAFYEIL HLPNLNEEQR NAFIQSLKDD
PSQSANLLAE AKKLNDAQAP KGSSVDNKFN KEQQNAFYEI LHLPNLNEEQ RNAFIQSLKD
DPSQSANLLA EAKKLNDAQA PKSGG 2)4_Z_ASP

MGSSHHHHHH SSGLVPRGSH MVDNKFNKEQ QNAFYEILHL PNLNEEQRNA FIQSLKDDPS
QSANLLAEAK KLNDAQAPKD DDVDNKFNKE QQNAFYEILH LPNLNEEQRN AFIQSLKDDP
SQSANLLAEA KKLNDAQAPK DDDVDNKFNK EQQNAFYEIL HLPNLNEEQR NAFIQSLKDD
PSQSANLLAE AKKLNDAQAP KDDDVDNKFN KEQQNAFYEI LHLPNLNEEQ RNAFIQSLKD
DPSQSANLLA EAKKLNDAQA PKDDD

Figure 10

MODIFIED ADSORPTIVE SURFACES

TECHNICAL FIELD

The present invention is directed to methods and formulations for producing analytical and preparative charge modified surfaces whose functions depend on both controlled affinity adsorption and desorption of target substances such as proteins. It is particularly well suited to development of chromatographic or analytical surfaces, which employ protein affinity ligands related to Protein A, G, or L.

BACKGROUND

Chemicals including both small molecular weight entities and larger entities such as proteins, often display significant affinity for other molecules and/or surfaces. Affinity interactions are particularly important in biology where their specificity and avidity form the basis for enzymatic reactions, transport functions, immune recognition and so on. Such interactions have found commercial use in regard to pharmaceutical, analytical and preparative applications. In regard to the latter two applications, various insoluble surfaces such as microtiter plates, sensor chip surfaces, filter surfaces, and chromatographic particle (resin) or monolith surfaces are often modified with affinity substances such as enzymes, immunoglobulins, enzyme substrates, antigens, or other entities with relatively high affinity for their "targets", e.g. an affinity constant of less than 1 millimolar (1 mM). An affinity of 1 mM indicates that when the target is at 1 mM concentration, in the presence of excess binding "ligand", over half the target molecules in solution will be bound. The greater the affinity, the lower the affinity constant, and the greater the ability of the interaction to be selective and to bind target from a complex mixture. The skilled person realizes the affinity constant varies with many factors including but not limited to ionic strength, pH, temperature, presence of further species in a solution and so on. The skilled person also realizes that insoluble molecular surfaces, such as those of responsive polymers whose solubility varies with temperature, conductivity, pH or other solution conditions, are often used as supports for ligand presentation.

The molecularly structured nature of biological molecules, and their related affinity interactions, mean that binding constants of less than 10 nanomolar (10 nm) are quite common and in some cases they can be several orders of magnitude lower. The ability to use such very high affinity interactions for analytical purposes requires both selective affinity binding and ease of target release—the latter allowing for the analytical surfaces to be reused. Localization of affinity "ligands", including oligopeptides or proteins, on various surfaces creates opportunities for non-specific adsorption of non-target entities—which may be proteins or other test solution components or contaminants including detergents, nucleic acids, carbohydrates, bacteria, virus, cells, cell debris, etc. It is well understood that such non-specific adsorption (often termed fouling) can be based on less specific, and often less molecularly oriented, interactions such as charge-charge, hydrogen bond, hydrophobic or van der Waals forces. The ability to use high affinity interactions for preparative purposes such as target purification and concentration, as in affinity chromatography or filtration, puts additional demands on the related "ligand support" surfaces which must offer good mechanical rigidity and solution pressure-flow properties, as well as high ligand density per support volume, and good chemical stability. Insoluble supports offering such properties may also readily foul, and major effort over the past fifty years has gone into developing modified versions of cross-linked polymeric (e.g. agarose, dextran, polyacrylamide, divinylbenzene) and other (e.g., silica) based supports which provide for reduced fouling. Nevertheless, fouling is still a major challenge. It reduces affinity, selectivity, target-binding capacity and can result in a need for harsh chemical cleaning-in-place (CIP) regimes, often involving NaOH solutions with high pH. The latter puts further demands on supports and ligands and ligand attachment chemistries that must withstand repeated CIP condition exposure.

Recombinant biopharmaceuticals approved for medical use now number close to 200 and several hundred are in phase trials. Most are proteins, but there are also nucleic acid, polymer-protein conjugates, antibody-drug conjugates (ADCs), bio-liposomal, cell-based and other biopharmaceuticals. Approximately 50 monoclonal antibodies (mAbs) have been approved in the US and Europe and almost all of them are purified by processes which include Protein A based affinity chromatography. mAbs account for approximately half of pharmaceutical sales and by 2020 it is expected that seventy mAb products may be on the market and account for total world-wide sales of 120 billion dollars per year. This relates to purification of hundreds of metric tons of mAb proteins (Ecker, D. M, Jones S. D., Levine, H. L., The therapeutic monoclonal antibody market. mAbs Journal, 7: 9-14, 2015). Purification process-related costs often account for one-third or more of the "cost of goods" related to producing such products. Continued improvement in the capacity, selectivity (purification ability) and "cost per gram of target" productivity of Protein A affinity ligand based processing is directly linked to the treatment cost of a wide range of biopharmaceuticals which favorably affect the lives of millions of patients.

Almost all commercial biopharmaceutical mAbs are produced using processes which include an affinity chromatography capture step based on chromatography particles whose surfaces are modified with Staphylococcal Protein A related ligands. Humira® may be the only notable exception. Such ligands typically bind mAb targets at neutral pH (e.g., pH 7) and release targets at acidic pH (e.g., pH 3). A single Protein A based affinity chromatography step (unit operation) is often used as the first capture step in a mAb purification process and can often purify the mAb target to >95% purity.

In addition to mAbs proteins related to mAbs such as Fc-fusion proteins, formed by recombinant fusion of mAb "Fc" regions to other proteins, or antibody fragments (Fabs) which often lack the Fc region, are emerging as important classes of therapeutic proteins, as are ADCs. Protein A based ligands bind antibodies via their Fc regions and so can be used to prepare analytical and preparative surfaces that show affinity for a wide range of antibodies and proteins modified with antibody Fc regions (so called Fc-fusion proteins). In a similar manner antibody fragments (Fabs), and some antibody subclasses that do not show affinity for Protein A based ligands, can be bound by other protein affinity ligands such as those related to Protein L and G. The conditions of binding and elution of Fabs from Protein L and G are similar to that of mAbs from Protein A based ligands although elution may require even lower pH (e.g., 2) (Rodrigo, G., Gruvegard, M., Van Alstine, J. M., Antibody Fragments and Their Purification by Protein L Affinity Chromatography, Antibodies 4(3): 259-277, 2015). The effectiveness of relatively low cost delivery of future mAbs, Fabs, ADCs and related biopharmaceuticals will be linked to efficiency of their affinity chromatography and other purification process steps in terms of capacity, purity, and efficient recovery of functional product. These proteins are typically produced in nonhuman cell lines so host cell protein (HCP) contamination is a significant health risk. In addition, any HCP contamination or the presence of aggregated target protein can enhance the immunogenicity of a pharmaceutical preparation and reduce its effectiveness as well as the duration over which a patient may use the preparation without developing serious side effects.

A typical binding ligand "affinity domain region" (ADR) from Protein A has an IgG affinity of approximately 10 nM (10×10EXP-9 moles per liter) which means that at an antibody concentration of 10 nM, 50% of the affinity binding sites should have bound protein, and under conditions of excess ligand most of the target protein sample can be bound. Often substantial chemical or recombinant modification of the binding ligand affinity domain region (ADR) can still result in a ligand with relatively high affinity (e.g. less than a 10× reduction in affinity) though results are difficult to predict. Many factors including protein sugar "glyco" groups, or structural integrity, can play a role in enhancing or degrading target affinity.

It is generally appreciated that recombinant modification of affinity proteins or related protein binding ligand affinity domain region (ADR) (regions) does not always result in affinity ligands that can be expressed, or purified, or are structurally or chemically stable to their intended surface coupling, or bioprocessing operating conditions.

Natural protein ligands must be covalently attached to a sensor or other (chromatography resin or filter) surface. Various covalent coupling methods (e.g. amide, ether, ester) are well known from the literature (Bioconjugation Techniques, Greg T. Hermanson, $3^{rd}$. Edn., Academic Press, N Y, 2013). In regard to Protein A based ligands, typical coupling methodology may include thiol-modified (activated) resin to which a ligand with a natural or recombinantly inserted cysteine or other thiol containing group is coupled via a chemically stable thio-linkage (Ljungquist, C., Jansson, B., Moks, T., Uhlén, M., Thiol-directed immobilization of recombinant Ig G-binding receptors, Eur. J. Biochem. 186: 557-561, 1989). The general resin coupling technology is common in regard to affinity (protein) ligand attachment both in regard to affinity resins and sensor surfaces. In some cases the surface activation procedure may generate excess reactive thiol groups that need to be "capped" by reacting with various simple chemical groups to prevent them reacting with surface localized target or HCP proteins.

FIG. 1 simplistically illustrates ideal solid phase protein affinity interaction with surface (black rectangle) immobilized ligand (cross hatched). Target protein (Y branched shaped liked an antibody) is bound at neutral pH and then under the binding conditions the surface is washed (dotted arrow) to remove unbound, non-target proteins or other contaminants (circles and triangles). The solution is then altered to eluting (i.e. non-binding) conditions such as pH 3 to elute target. This allows recovery of pure target and the surface to be ready for reuse. In the example shown the affinity ligand is a protein, such as a Protein A related Ab binding ligand affinity domain region (ADR) region, and it binds one (antibody) target molecule. Affinity-sensors, -chromatography resins, -filters, -microtiter and -array assays, often involve similar phenomena. FIG. 2 presents the same illustration under more realistic conditions with some non-affinity contaminants interacting with underlying surface or affinity ligand or bound target protein. The solution is then altered to elute target, which may elute with contaminants. Further CIP treatments may be required for the surface to be reused. FIG. 3 shows a typical chromatogram related to purifying clarified (cell and particle free) fermentation feed using Protein A ligand based affinity chromatography. For more explanation see Pabst, T. M., Palmgren, R., Forss, A., Vasic, J., Fonseca, M., Thompson, C., Wanga W. K., Wanga, W., Hunter, A. K., Engineering of novel Staphylococcal Protein A ligands to enable milder elution pH and high dynamic binding capacity. J. Chromatogr. A 1362: 180-185, 2014. Most clarified feed contaminants will not adsorb and will therefore "flowthrough" under loading and washing conditions (e.g. pH 7) with relatively pure target protein being eluted with some contaminants (e.g. HCP or mAb aggregates) at pH 3. Loading is typically done under relatively high conductivity (e.g. 0.15-0.30M NaCl containing buffer). Elution is typically conducted under lower conductivity. Remaining (fouling) protein is then "stripped" from the column under harsher chemical conditions.

Native Protein A molecules may exhibit multiple (e.g., five) target binding ligand affinity domain region (ADR) regions; each one capably of binding one antibody molecule (Hober, S, Nord, K., Martin Linhult, M, Protein A chromatography for antibody purification, J. Chromatogr. B 848: 40-47, 2017). Due to steric interactions, and other reasons currently not well understood at present, typically only one to two antibodies bind to each Protein A ligand, although more ligand affinity domain regions (ADRs) are available with a theoretic potential to bind perhaps twice as much antibody. Different ligand affinity domain regions (ADRs) vary slightly in structure and binding as well as chemical stability and other desired properties. Ghose et al., reported that a native Protein A based affinity resin (MabSelect™, GE Healthcare) eluted a test panel of IgG and Fc-fusion proteins over a pH range between 3 and 4 (i.e. a 10× difference in hydrogen ion concentration) whereas a, Protein A related antibody binding ligand affinity domain region (ADR) termed Z (MabSelect SuRe™, GE Healthcare) in tetravalent Z4 configuration on a similar agarose base matrix (Hober et al., 2007.), eluted the same panel of test target proteins, in a different order, over the pH range 3.6 to 4 (only a 2.5× difference in hydrogen ion concentration) (Ghose, S., Hubbard, B., Cramer, S. M., Binding capacity differences for antibodies and Fc-fusion proteins on Protein A chromatographic materials, Biotech. Bioeng. 96: 768-779, 2007). In that example Z had been recombinantly modified to enhance chemical CIP stability and the recombinant ligand modifications undertaken to enhance chemical stability also fortuitously improved performance by reducing the expected range of elution conditions which operators had to evaluate during process optimization. Such evaluations are not only performed to optimize a unit operation but must be carried out in order to achieve the understanding and control over the unit operation which national drug licensing offices demand.

A collaboration between MedImmune and GE Healthcare (Pabst, et al.) studied effects of recombinant modifications of the Z based MabSelect SuRe (GE Healthcare) affinity chromatography resin. Two Z residue modifications (a histidine to a less acidic serine which would be neutral at pH≤9, and a "double" modification of both histidine to a less acidic serine plus an asparagine to a less basic and neutral alanine) were noted. Both sets of mutations are expected to reduce the net charge nature of the Z ligand affinity domain region (ADR) at neutral pH (commonly used for loading). As noted above, the ability of the ligands to be expressed, purified, surface coupled and used in the intended manner was a prerequisite to consideration of their chromatographic behavior, and possible commercial usefulness. The modifications resulted in target elution at approximately 0.5 units higher pH with significantly greater elution recovery (30%) of test proteins at pH 4. Total affinity resin binding capacity and selectivity were not compromised. It was also noted that pH 4 versus pH 3.5 elution can favor recovery of less aggregated target. These major companies appeared to view these results as significant in regard to product recovery and "cost of goods" and perhaps also in regard to biopharmaceutical target efficacy.

Protein A based affinity chromatography can result in a 98% pure product in the initial capture step of a standard mAb purification process. However some people consider it expensive in regard to mAbs purified per ligand, and the time involved in various washing and regimes. In a study of user satisfaction with various biopurification methods Tran et al. found that Protein A based affinity chromatography was only graded 80/100 suggesting that more improvement is desired (Tran, R., Zhou, Y., Lacki, K. M., Titchener-Hooker, N. J., A methodology for the comparative evaluation of alternative bioseparation technologies. Biotechnol. Prog., 24: 1007-1025, 2008).

Several scientific groups (e.g., Shukla et al., Bracewell, Rathore et al., Lenhoff et al., Carta et al.) have elucidated the nature of host cell proteins and other contaminants, such as nucleic acid related entities, that may foul affinity surfaces or co-elute with immunoglobulins from Protein A based affinity chromatography columns. Two recent references are: Zhang, S., Daniels, W., Salm, J. Glynn, J., Martin, J., Gallo, G., Godavarti, R., Carta, G., Nature of foulants and fouling mechanism in the Protein A MabSelect resin cycled in a monoclonal antibody purification process, Biotechnol. Bioeng. 113: 141-149, 2016; and Levy, N. E., Valente K. N., Choe, L. H., Lee, K. H., Lenhoff, A. M., Identification and characterization of host cell protein product-associated impurities in monoclonal antibody bioprocessing. Biotechnol Bioeng. 111: 904-12, 2014. In regard to Protein A ligand based affinity chromatography the results from several studies are similar, synergistic, and can be summarized as follows:

a. HCP and related contaminants accumulate during loading and are often associated with target.
b. The amount of co-eluting HCP varies directly with bound and eluted antibody.
c. Co-Eluting HCPs tend to be of lower MW (<70 kDa) than target antibody and also acidic (negatively charged at pH 7) with pI's often in the general range 3 to 6.
d. HCPs with pI in range 6-8 (so neutral under loading conditions) did not typically bind on the column or co-elute with target.
e. Different Protein A based affinity resins, from different vendors, featuring very different base matrices (i.e., silica, cross-linked agarose, polymethylmethacrylate) show similar results, suggesting that similarities in various vendors' ligands, as well as in pharma companies' mAb-related targets molecular structures play important roles.
f. Fc-fusion proteins (which are not Abs, but often exhibit similarly high pI's 8-10) show similar results.
g. Low pH 3 desorbtion may enhance retention of the Ab-HCP complexes on the surface.

Table 1 indicates the net charge of mAbs, Fabs, ADCs and related targets; as well as Protein A, L and G ligands, and related ligand affinity domain regions (ADRs); and expected host cell proteins (HCPs) and other contaminants under typical affinity binding (loading), wash and elution conditions. In general, the ligands and contaminants are net negatively charged under loading while the targets are net positive. This helps reduce, but does not eliminate, nonspecific contaminant surface adsorption and ligand interaction. At the same time, the net charge states are expected to enhance "long range" target-contaminant interactions and promote ease of affinity binding. Under elution conditions (e.g. pH 3) the ligand is expected to be neutral or net positive, as are many contaminants and target proteins. However at such low pH, target proteins may also be structurally unstable, and prone to aggregate, and surface localize. Many authors have noted that such aggregation can be reduced if elution is achievable at a higher pH (e.g., Pabst et al.). These charge nature surface effects are simplistically illustrated in FIG. 4. Similar considerations apply for many other targets and affinity ligands (see text). Other contaminants can be detergents, virus, cell debris, bacteria, etc.

TABLE 1

Expected pI and Net Charge of Affinity Targets, Host Cell Proteins, Protein A Related Ligands, and Other Contaminants Under Typical Load, Wash and Elute Conditions Used in Protein A Based Affinity Chromatography

| Proteins or Other | pI's | Load* 0.15M NaCl pH 7 | Wash** 0.1-0.5M NaCl, pH 7 | Elute 0.1-.05M NaAc, pH 3-3.5 | Ideal Elute 0.05M pH 4-5 |
|---|---|---|---|---|---|
| mAbs or Fabs or ADCs | 8-9 | + | + | + | + |
| Most HCPs | 3-8 | Attract Mostly− | Attract Mostly− | Mostly+ | +/− |
| Protein A *** | 5-6 | − | − | + | +/− |
| Other Contaminants | 3-6 | − | − | +/− | +/− |

*20 mM NaP.
**Primary wash is often in load buffer or equivalent, can be pH 6. High mS/cm promotes hydrophobic interaction, van der Waals forces, and weakens electrostatic interactions.
*** Approx. similar for Protein A, L, G and their ligand affinity domain regions (ADRs).

The proteins which are bound and not washed away but co-elute (or may remain and require more active cleaning-in-place) are often small negatively charged proteins. Some may interact with mAbs in solution but such interactions, which must also occur in plasma but normally do not lead to stable protein-protein complex formation to an appreciable degree, may involve short range interactions and require protein localisation and concentration at a surface to become energetically stable. Such HCP's will diffuse faster than mAbs and are generally expected to reach the surface prior to mAbs. Protein pI values only represent net sum gain for the entire protein. It is well recognized that all proteins contain positive, negative and hydrophobic surface regions and the localized contaminants will be available to readily find favorable interactions with bound target molecules which may not be eliminated by "normal" pH 7 washing in loading buffer or higher conductivity buffer. The resulting target-HCP or target-target interactions may then promote complex or aggregate formation under the low pH conditions required for target elution. The fact that some HCPs elute with mAbs from ion exchange, hydrophobic affinity and mixed mode resins (Levy et al., 2015) also suggest that the phenomena may involve various forces of interaction which are not unique to affinity chromatography.

Similarities in results from the HCP co-elute studies noted above also suggest that methods to reduce weak, nonspecific, contaminant-surface interactions may reduce such undesired consequences. In addition such similarities suggest that successful solutions to this problem may be universally applicable to a wide range of affinity chromatography and related affinity applications. This includes affinity interations based on "protein A mimetics" (e.g., Roque, C. A., Lowe, C. R., and Taipa, M. A., Antibodies and genetically engineered related molecules: Production and purification, Biotechnol. Prog. 20: 639-654, 2004).

The following Table 2 presents an overview of different surface modifications which might be undertaken to improve affinity capture and release. This analysis led the inventor to decide that Modification type 3 appeared to be the most promising.

| | Modification | Approach | Expected results |
|---|---|---|---|
| 1 | Lower surface pI | Covalently attach acidic group (e.g. mercapto propionic acid reacting with surface-SH) | May reduce negative HCP adsorption May allow target elution at higher pH May reduce high pH CIP effects on resin Resin may exhibit ion exchange as well as affinity binding site |
| 2 | Lower ligand pI | Modify ligand amino acid sequence to reduce pI | As in 1 above Could affect target affinity and release |
| 3 | Lower ligand tether pI Also regions linking domains | Modify tether amino acid sequence to reduce pI Use polyacid or other non-protein tether | As in 2 above Expect less effect on ligand binding site affinity Easier to incorporate into ligand |
| 4 | Low fouling surface polymers | Neutral hydrophilic polymer PEG-SH capping of surface SH-groups | Reduce nonspecific fouling but could affect resin pressure flow properties, affinity ligand and target elute. Some polymers may not be CIP stable thus reducing the CIP stability and production life-time of the affinity product. |
| 5 | Lower surface pI with other non-fouling modifications | Covalent link non-fouling zwitterionic groups that also buffer in desired range. E.g. betaine type chemicals Achieve similar result with zwitterionic polymer or mixture of reagents | Reduce negative HCP non-specific adsorption May allow target elution at higher pH May reduce target aggregation May reduce high pH CIP effects on resin |
| 6 | Various combinations of 1 to 5 above, such as approaches 4 and 5. | As above. | As above. |

One major challenge faced in constructing affinity surfaces is to incorporate a high surface density of ligands in a manner that does not enhance "nonspecific" adsorption of non-target substances, which can lead to incomplete bioprocess purifications, surface fouling, and inaccurate analytical results. Another major challenge is to develop surfaces that allow easy and improved release of bound target substances. The latter not only ensures the ability to reuse the surfaces, but also to recover target substances in an unaltered state. Normally such challenges might be dealt with by reducing (not increasing) the charge nature of the surfaces and ligands. However charges are often contributed by low molecular weight (e.g., $M_W<300$ Da) organic "spacer" groups which are used to link various surfaces to low or high MW ligands via amide or other charged groups (see Hermanson, 2013.)

US 2016168229 discloses an affinity chromatography matrix comprising particles surface linked with blood group oligosaccharide epitopes analogues via low MW organic spacer groups (which may contain charge groups, see Hermanson, 2013). Such surfaces can bind antibodies directed at the appropriate blood group epitopes via immunoaffinity interaction.

WO 98/08603 discloses purification of immunoglobulins using an insoluble solid phase to which low MW spacer groups have been used to link mixed mode ligands composed of non-charge-based aromatic groups and charged organic acidic groups. It should be noted that the role of the charged groups is to bind antibody target via electrostatic interactions, and that such mixed mode ligands are expected to bind one antibody per ligand.

WO 2013/117707 also concerns purification of antibodies by mixed mode chromatography using a different set of aromatic (and hetero-aromatic) group containing ligands whose structures also include charged groups. It should be noted that the role of the charged groups is to bind antibody target via electrostatic interactions, and that such mixed mode ligands are expected to bind one antibody per ligand.

Liu et al., J. Chrom. 792, 177-185, 2003 relates to sulfamethazine ligands for binding antibodies and includes standard spacer chemistry that can contain charged organic chemistry groups like acids or hydroxyls.

Zamolo, L., et al in J. Phys. Chem. B, 114: 9367-9380, 2010 undertook a theoretical and experimental investigation of the effect of spacer arms and matrix on the performance of synthetic affinity ligands for the purification of monoclonal antibodies.

In the above examples low MW spacer groups may have provided charged molecules as part of the their linking function, or charge groups may have been included in the ligand to effect charge dependent (e.g. ion exchange type, low conductivity) binding of target as part of a mixed mode ligand based interaction. Of course simple ion exchange ligands are often used to bind antibodies or other targets (Harinarayan, C., Mueller, J., Ljunglof, A., Fahrner, R., Van Alstine, J., van Reis, R., An Exclusion Mechanism in Ion Exchange Chromatography, Biotechnology and Bioengineering, 95: 775-787, 2006). None of the above charge variations relate to affinity ligands for use in binding antibodies and related targets. Also as noted recombinant alterations to affinity ligands or individual binding domain regions, such as protein A related Z binding domains, have often involved development of less charged domain variants.

Gräslund, T. et al., generated mutant Z binding domain ligands which exhibited greater positive surface charge, in the ADR, in order to aid ligand purification via cation exchange chromatography. They demonstrated that such Protein A domain-related, charge-enhanced mutants could be expressed and produced in *E. coli* fermentation, maintained native structure similar to Z, and could be recombinantly fused with other proteins such as the albumin binding domain related to Protein G (Gräslund, T., Lundin, G., Uhlén, M., Nygren, P. A., Hober, S., Charge engineering of a protein domain to allow efficient ion-exchange recovery, Protein Engineering, 13: 703-709, 2000).

US20100221844 Caustic stable chromatography ligands provides for an alkaline-stable (i.e. basic pH CIP stable) chromatography ligand which comprises two or more binding domains based on *Staphylococcus* Protein A (SpA), or a functional fragment or variant thereof, where the ligands are attached to a chromatography resin at more than one site on the resin. This patent also presents CIP stable mutants where binding domain position 24 specific residues of glutamic or aspartic acid have been recombinantly replaced with a wide range of other residues including phenylalanine, threonine, proline, tryptophan, valine, tyrosine, lysine or arginine residues (patent ref. Table 1). In US20100221844 some examples relate to ligands with three binding domains from Protein A such as three A (AAA) or three D (DDD) or three E (EEE) domains. These patent specific abbreviations should not be confused with the official scientific designation for a sequence of three alanine (AAA), three aspartic acid (DDD) or three glutamic acid (EEE) residues, as used world wide in regard to identifying protein amino acid residues, and in the present patent application.

It is desirable to increase the binding capacity and provide a surface with improved ability to release bound target substances during for instance protein purification. For that reason GE Healthcare recently launched a new Protein A based affinity chromatography resin (PrismA™) which utilizes six engineered Z-type domains per ligand versus the four used in MabSelect SuRe the present industrial Protein A based resin of choice. This 50% increase in domains per ligand apparently only increased dynamic binding capacity by approximately 25% (see FIG. 3 in J. Royce, Reimagining capacity for today's purification of monoclonal antibodies, Bioprocess International, 16: 9-19, 2018). Research to develop improved binding domains which offer target selectivity (i.e., nM affinity), improved capacity and elution at higher pH continue. The work of Pabst et al. was noted previously. Strauch et al. summarized the general directions of such research, "Previous efforts to engineer pH-dependent protein switches have either used structure-guided insertion of ionizable groups or systematic histidine scanning mutagenesis. These approaches often result in lower affinity interactions or low sensitivity to physiologically relevant pH changes." (Strauch E.-M., Fleishman, S. J., Baker, D., Computational design of a pH-sensitive IgG binding protein, Proceedings of the National Academy of Sciences, 111: 675-680, 2014). It is noteworthy that all of the above efforts relate to the charge nature of added or removed residues, but not to their local molecular surface buffering capacity, or ability to enhance affinity surface target localization, or how the buffering effect of added basic or acidic residues may counteract the effect of binding a single target, whose pI differs significantly from the optimal binding pH of the binding domain, on the ability of multi-domain ligands to bind additional targets.

SUMMARY

It is an object of the present invention to obviate at least some of the disadvantages in the prior art and provide an improved adsorptive insoluble surface (IS) as well as a method of purifying a substance and a method of manufacturing the adsorptive surface.

In a first aspect there is provided an adsorptive insoluble surface (IS) for binding "at least one substance", said insoluble surface (IS) comprising a plurality of ligands (L), each ligand comprising n ligand affinity domain regions (ADR), wherein n is at least two, wherein each ligand affinity domain region (ADR) has the ability of specific binding of at least one of the at least one substance, wherein one first ligand affinity domain region (ADR 1) is bound to the insoluble surface (IS) with a ligand to insoluble surface attachment region (SAR) and wherein ligand affinity domain region (ADR n) is bound to ligand affinity domain region (ADR n–1) with a ligand ADR joining region (AJR), wherein at least the ligand ADR joining region (AJR) comprises at least one selected from the group consisting of at least one charged group ($C_{AJR}$) and a noncharged link ($N_{AJR}$).

In a second aspect there is provided a method of isolating at least one substance from a liquid comprising the steps of:
a) contacting the liquid comprising the at least one substance with the adsorptive insoluble surface (IS) as described above, under conditions where each ligand affinity domain region (ADR) has the ability of binding the at least one substance,
b) optionally washing the adsorptive surface,
c) eluating the at least one substance under conditions where each ligand affinity domain region (ADR) has reduced ability of binding the at least one substance.

In a third aspect there is provided a nucleic acid encoding a recombinant protein, said protein comprising n ligand affinity domain regions (ADR), wherein n is at least two, wherein each ligand affinity domain region (ADR) has the ability of specific binding of at least one of the at least one substance, wherein one first ligand affinity domain region (ADR 1) is bound to the insoluble surface (IS) with a ligand to insoluble surface attachment region (SAR) and wherein ligand affinity domain region (ADR n) is bound to ligand affinity domain region (ADR n–1) with a ligand ADR joining region (AJR), wherein at least the ligand ADR joining region (AJR) comprises at least one selected from the group consisting of at least one charged group ($C_{AJR}$) and a noncharged link ($N_{AJR}$).

In a fourth aspect there is provided a protein expression system comprising the nucleic acid as described above. The protein expression system is any known and suitable protein expressing system capable of expressing the desired protein for the present invention to be used as a ligand.

In a fifth aspect there is provided a method of manufacturing an adsorptive insoluble surface (IS) as described above, the method comprising binding a ligand to the surface using a ligand to insoluble surface attachment region (SAR). The ligand is attached to the surface using any known and suitable method.

Further aspects and embodiments are defined in the appended claims, which are specifically incorporated herein by reference.

An advantage is an increased binding capacity for the desired molecule.

One advantage is that non-specific binding of negatively charged host cell protein to a more negatively charged resin surface is expected to be reduced (e.g., see Table 1 in Malmsten, M., Lassen, B., Van Alstine, J. M., Nilsson, U. R., Adsorption of Complement Proteins C3 and C1q, J. Colloid Interf. Sci., 178: 123-134, 1996).

Another advantage is that the addition of the charged buffering groups should allow for less variation in optimum pH for elution at least in some embodiments. Further the elution pH in some conditions is less acidic and thereby milder.

BRIEF DESCRIPTION OF THE DRAWINGS

The invention is now described, by way of example, with reference to the accompanying drawings, in which:

FIG. 5 schematically shows three different ligand constructs each with four Z binding domains. There is shown different ligand constructs including (A) a tetravalent four Z ligand affinity domain region (ADR) ligand with possible surface attachment via one terminal His-6 end, binding ligand affinity domain region (ADR), ligand affinity domain region (ADR) joining regions and (optional) solution exposed free terminal region. (B) a similar "ASP" tetravalent ligand charge enhanced in the non-affinity attachment, joining and solution exposed terminal regions. (C) a similar tetravalent "GGS" ligand which in an experimental control was modified with non-charge residues in the non-affinity attachment, joining and solution exposed terminal regions.

FIG. 10 shows amino acid sequences of two Z-domain variants similar to those in FIG. 5. (1) Amino acid sequence of 4_Z_GGS ligand. Four Z-domains and C terminal were linked via combinations of three neutral Glycine and Serine molecules. N-terminal of the protein has a cleavable 6-Histidine tag to aid purification. (2) Amino acid sequence of an analogous 4_Z_ASP ligand with three Aspartate (D) residues added in the binding domain joining, and C terminal regions.

DETAILED DESCRIPTION

Figure 1:
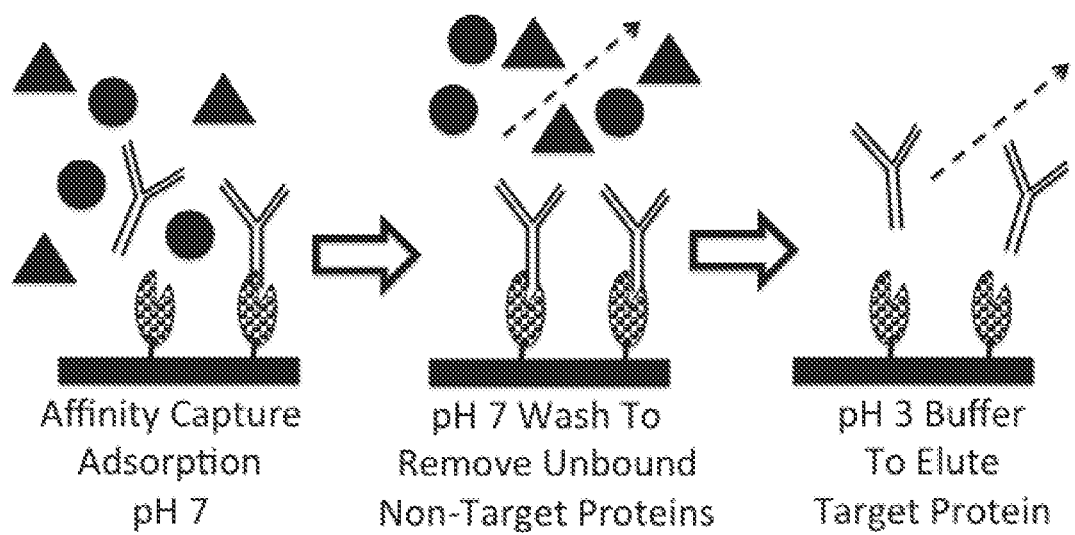
FIG. 1 illustrates ideal solid phase protein affinity interaction with surface immobilized ligand (cross hatched). Target protein (Y shaped) is bound and then under binding conditions surface is washed (dotted arrow) to remove unbound, non-target proteins or other contaminants (circles and triangles). The solution is then altered to nonbinding conditions to elute target. This allows recovery of relatively pure target and the surface to be readied for reuse. In the example shown the affinity ligand is a protein ligand which binds one target molecule. Affinity-sensors, -chromatography resins-filters, -microtiter and -array assays, often involve similar phenomena.
Figure 2:
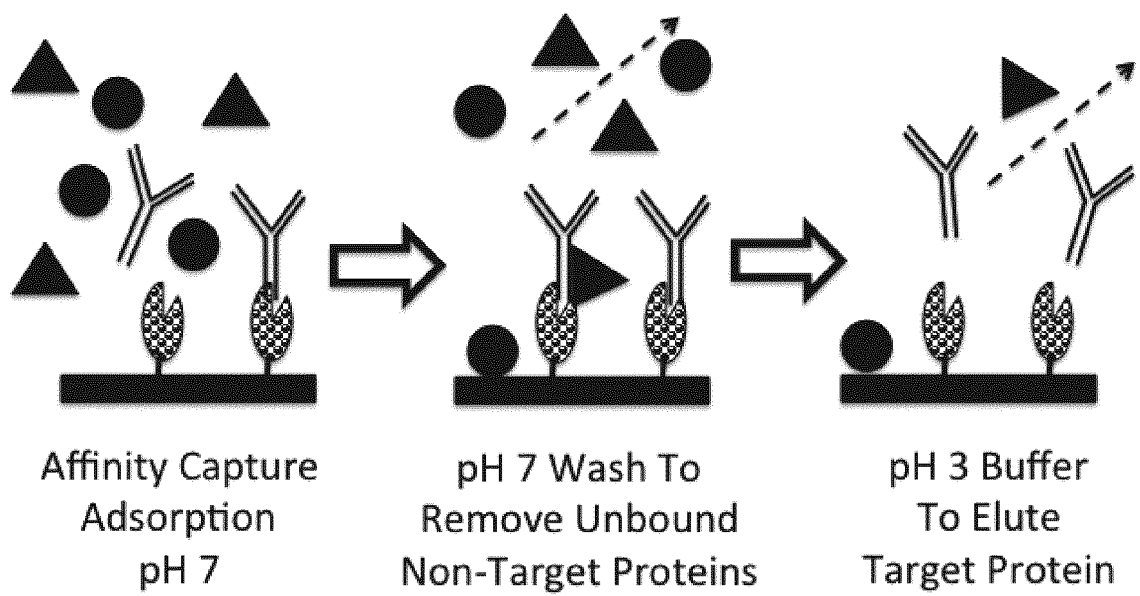
FIG. 2 shows non-ideal solid phase protein affinity interaction with surface immobilized ligand (cross hatched). Target protein (Y shaped) is bound and then under binding conditions surface is washed (dotted arrow) to remove unbound, non-target proteins or other contaminants (circles and triangles). However some contaminants interact with underlying surface or affinity ligand or bound target protein. The solution is then altered to nonbinding conditions to elute target, which may elute with contaminants. Further cleaning under harsher "strip" conditions may be required for the surface to be reused.
Figure 3:
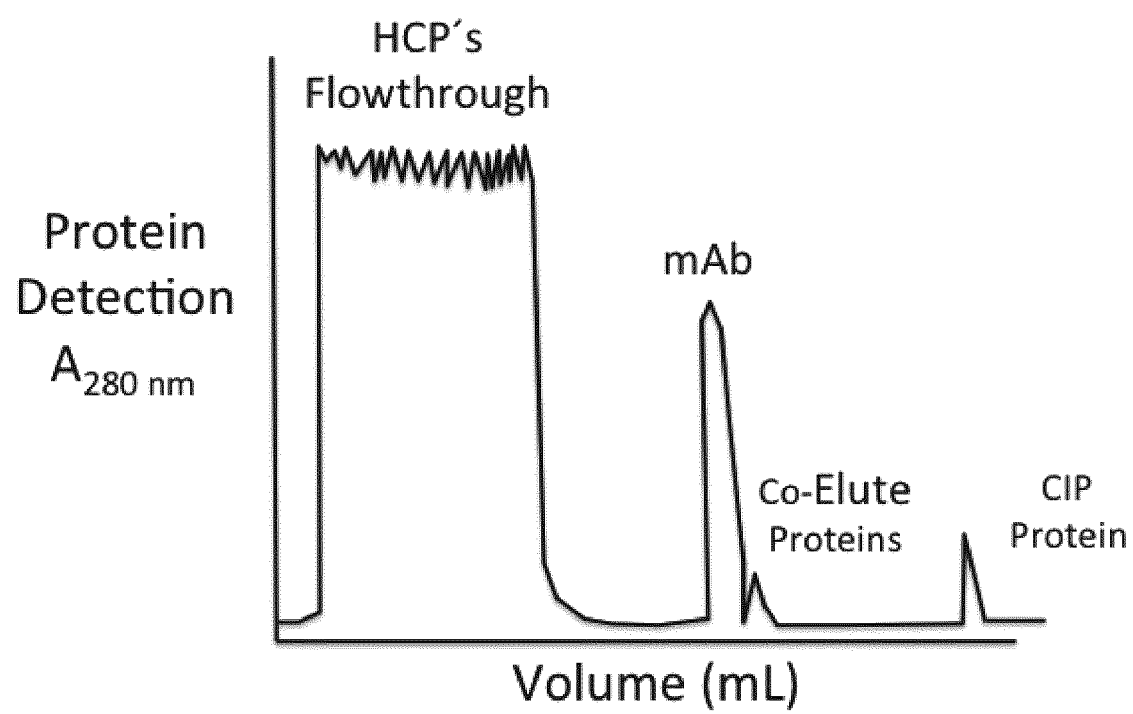
FIG. 3 shows typical Protein A resin based affinity chromatography capture and recovery of monoclonal antibody (mAb) from clarified fermentation feed. mAb is loaded at perhaps 30 g/L flow rate to allow for 4-6 min column flow through residence time. Equilibration Buffer (EB) of 0.15M NaCl, 20 mM NaPhosphate, pH 7, Load mAb to 1% breakthrough (defined as a UV280 nm absorbance which one hundredth the absorbance associated with the target load sample), Wash 5 column volumes (CV) of EB, then elute mAb and any co-eluting proteins with (1-2 CV) 50 mM NaAcetate, pH 3.5. Finally strip residual nonspecifically bound protein with cleaning in place (CIP) at high pH (e.g. 0.1M NaOH).
Figure 4:
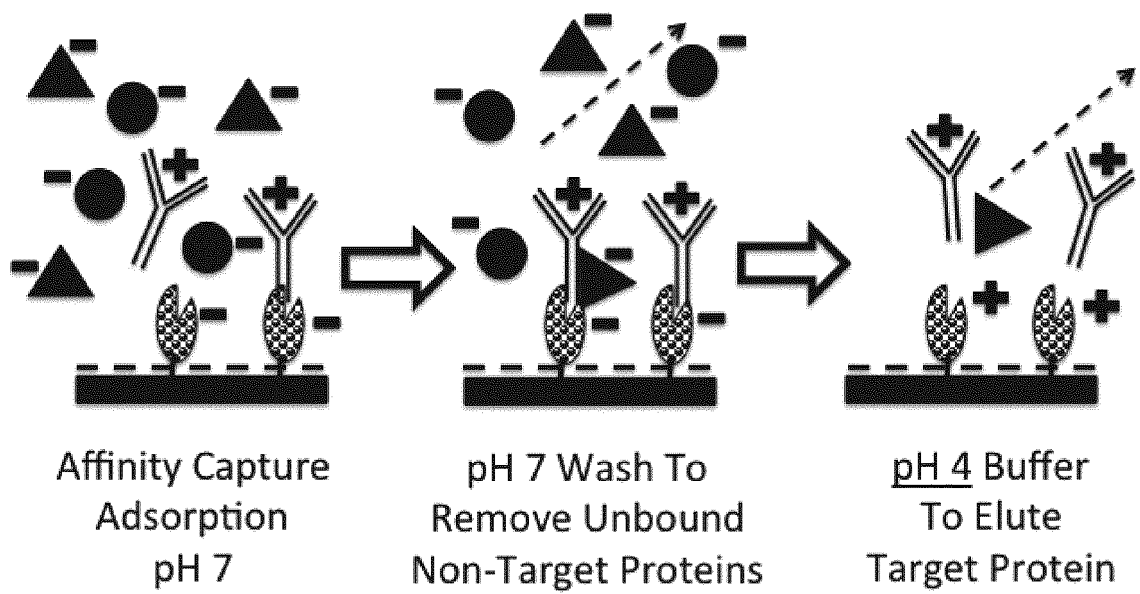
FIG. 4 shows non-ideal (more realistic) solid phase protein affinity interaction with surface immobilized ligand (cross hatched) and modified with acidic buffering residues. Target protein (Y shaped) is net positive. Ligand and contaminants are net negative. Target is bound and then under binding conditions surface is washed (dotted arrow) to remove contaminants (circles and triangles). Some contaminants interact with affinity ligand or bound target protein. However the solution is rendered nonbinding at higher pH where contaminants show less interaction with target or surface and target aggregation may be reduced. In some cases the surfaces may also be modified with nonfouling surface coatings (dashed line above the surface). Affinity sensors, affinity chromatography resins, affinity filters, affinity microtiter and affinity array assays, may benefit from similar phenomena. Challenge is to find a buffering, nonfouling, easily used coating.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

Charged group as used throughout the description and the claims denotes a group of atoms in a molecule with a net charge. It is conceived that the charge depends on external factors such as the pH. At a certain pH the charge may be close to zero but when the pH changes the charge may change gradually until it may reach a value of for instance +1 or −1. A charged group has an absolute value of the charge of at least 0.9. Thus the charge of a negatively charged group must be at least −0.9 and the charge of a positively charged group must be at least +0.9. Thereby it is possible to determine if a group is charged or not for all conditions.

Insoluble surface (IS) as used throughout the description and the claims denotes solid matter to which the ligand is attached by a ligand to insoluble surface attachment region (SAR). One non-limiting example of such solid matter is the surface of an object which object is not soluble in a surrounding medium. Further examples include but are not limited to a part of a surface intended for an enzyme-linked immunosorbent assay (ELISA), a part of the stationary phase in affinity chromatography, a chromatographic resin, a chromatographic monolith, a chromatographic fiber, a chromatographic filter, a responsive polymer, a sensor chip, a microtiter plate, and so on depending on the application. It will be appreciated that protein SARs and surfaces may be covalently connected by low MW (<300 kDa) organic coupling agent spacers which are well known, some of which may contain charge groups such as amines (G. T. Hermanson, 2013).

Ligand as used throughout the description and the claims denotes a molecule with the ability to bind other substances. The ligands will also have ligand affinity domain region (ADR) regions, which may also be referred to as binding regions. Several such ligand affinity domain region (ADR) may be linked together to allow a ligand to bind multiple similar or dissimilar affinity targets, i.e. substances. The ligand affinity domain region (ADR) themselves may differ. For example, native Protein A has five slightly different binding regions while other non-native versions of Protein A based ligands often comprises four or six identical ligand affinity domain region (ADR) derived from one of the native Protein A ligand affinity domain regions. This is also applicable for ligands based on protein L or G or other affinity proteins. It is also true for hybrid ligands such as those which offer both A and G binding regions in the same ligand, or synthetic ligands containing more than one mimetic binding site. In all such cases, the functional affinity regions of the ligand can be thought of as joined together by structural ADR joining region (AJR)s. For ease of expression or purification or other reasons, the ligands may also have identifiable structural (non-affinity function) terminal regions, i.e., a ligand solution terminal region (STR).

Ligand affinity domain region (ADR) denotes a region in the ligand with the ability of binding at least one substance. In most embodiments the binding is specific for the desired substance so that the ADR binds to the intended substance but not to other substances. The letter n refers to the number of the ADR. It is conceived that the ADR number 1 is attached to the insoluble surface and that ADR number 2 is attached to ADR number 1. ADR number n is attached to ADR number n−1. Thus a chain of consecutive ADRs is created with AJRs between each ADR. There are at least two ADRs in the present invention.

Ligand ADR joining region (AJR) as used throughout the description and the claims denotes a molecule or a part of a molecule between two ligand affinity domain regions (ADR) joining the two ADRs together.

Ligand to insoluble surface attachment region (SAR) as used throughout the description and the claims denotes a part of a molecule that attaches the ligand to the insoluble surface (IS).

Ligand solution terminal region (STR) as used throughout the description and the claims denotes at least one end region of the ligand furthest away form the insoluble surface (IS). If the ligand is a chain-formed molecule such as a protein, then the STR is a free end not attached to the insoluble surface (IS).

It is to be appreciated that several obvious multi-domain ligand variations can be constructed and these might include branched ligands which offer more than two terminal groups. Likewise it is possible that ligands can be attached to surfaces by more than one terminal group.

Without wishing to be bound by any particular scientific theory the inventor believes that adding charge groups, in the AJRs of pKa opposite in acid-base nature to that of the pI of the target protein contribute to an overall attraction between the at least one substance and the ADR. The forces between the at least one substance and the ADR is a sum of many different attractive and repulsive forces including both electrostatic forces and other more short ranged forces as well as entropy. During a capture phase i.e. under conditions where each ligand affinity domain region (ADR) has the ability of binding the at least one substance, the net force should be attractive. However the nature of a ligand changes as one or more target substances are bound and it becomes a ligand-target complex whose pI and related local molecular region pH reflects the pI of the complex not the ligand which can be an order of magnitude smaller in MW than the target. During an elution phase, i.e. under conditions where each ligand affinity domain region (ADR) has reduced ability of binding the at least one substance, the net force should be less attractive compared to the capture phase or preferably even repulsive. However under such conditions added acidic groups may be protonated and uncharged.

Again, without wishing to be bound by any particular scientific theories the inventor believes that the specific affinity binding between an ADR and the at least one substance is due to a range of reasonably well understood molecular interactions whose pH related disruption leads to target release and that similar interactions occur not only in regard to Protein A based ligands but other ligands (e.g. Liu, F. F., Huang, B., Dong, X.-Y., Sun, Y., Molecular basis for the dissociation dynamics of Protein A-immunoglobulin G1 complex, PLoS ONE 8(6): e66935, doi:10.1371/journal.pone.0066935). As such it makes sense that changes in ligand binding domain molecular local pH, occurring following binding of target, which is larger and contains more residues than the binding domain, may affect the subsequent binding of target to other proximal domains. For example in the case of protein A or G binding an immunoglobulin of pI>8 (which is typical for this class of proteins) the local surface (ligand vicinity) pH may become more basic which may result in reduced affinity. Indirect evidence for this comes from Table 3 which shows how IgG binding is reduced as pH increases above 7.

TABLE 3

Effect of pH on the Binding of Human IgG by Protein A or G

| | pH | | | | | |
|---|---|---|---|---|---|---|
| | 3 | 6 | 7 | 8 | 9 | 10 |
| | | | % of Human IgG Bound Under Conditions Studied* | | | |
| Protein A | 1 | 2 | 21 | 27 | 14 | 12 |
| Protein G | 2 | 14 | 30 | 26 | 23 | 10 |

*Data from FIG. 10 in Bo Åkerström, Lars Björk, A Physicochemical Study of Protein G, a Molecule with Unique Immunoglobulin G-binding Properties, J. Biol. Chem., 261: 10240-10247, 1986. Peak position pH noted in boldface. Ref. indicates similar results seen with several other mammalian species IgGs.

Plausibility that bound IgG's can affect local surface pH comes from the buffering capacity of antibodies, which has been studied in regard to antibody drug formulation if not affinity chromatography. Karow noted that at 220 mg/ml volume, which we expect protein A bound mAbs to exceed in the molecular vicinity of chromatography resin surfaces, resembles 30 mM citrate (Karow, A. R., Buffer capacity of biologics—from buffer salts to buffering by antibodies Biotechnol Prog. 29:480-92, 2013. doi: 10.1002/btpr.1682).

Addition of charged residues to balance target binding alterations in local pH may offer other advantages. It must be noted that the substance has to come close enough to the ADR for the short range specific binding to occur. The probability for a substance molecule to be close to the ADR is less compared to being in the bulk of the solution because of the entropy. Fewer states for the substance molecule are available when being close to the ADR resulting in a lower probability of being close to the ADR compared to being in the bulk according to the Boltzmann distribution. An attractive electrostatic interaction force between the substance molecules and the ADR would thus increase the probability of the substance molecules being close to the ADR and achieving favorable affinity binding. A higher fraction of substance molecules closer to the ADR would thus enhance the probability of obtaining a specific binding of the substance molecule to the ADR, since the forces responsible for the specific binding are mainly short range. However there is a balance, since too high an attractive electrostatic force between the substance molecules and the ADR may not be desired. However normal conditions for target binding by protein affinity ligands often involve relatively high conductivity buffers which may attenuate such undesired complications. Simple molecular modeling of protein net charge and pI versus amino acid sequence studies (see Examples) suggest that by adding 2-10 charges in the AJRs, i.e. between the ADRs, there should be a good balance between the forces and the short range forces are enhanced without problems with unspecific binding. The added charges should have the opposite sign as the substance to be bound at the conditions (pH etc.) for binding, and be neutral or the same net charge as target at elution. The charges can be changed by changing pH for elution. Electrostatic forces can also be reduced for instance by increasing the ionic strength (conductivity) etc. It should be noted that one advantage of the above approach is that for an antibody or related target use of a more acidic ADR should result in reduced interaction with acidic host cell proteins and other net negatively charged contaminants (Table 1).

In regard to bioprocessing using Protein-A, -G or other affinity ligands, targets such as antibodies are typically adsorbed (loaded) onto a column at one pH and eluted at a lower pH. In some cases gradients of pH or ionic strength may be used to enhance the selectivity of the elution step, e.g., to isolate target from target aggregates. The revelation provided by considering the effect of target binding on local surface (ligand vicinity) pH suggests that improved target loading (i.e., mg of target per mL of packed resin) may also benefit from changes in adsorption buffer pH or ionic strength during loading.

In a first aspect there is provided an adsorptive insoluble surface (IS) for binding at least one substance, said insoluble surface (IS) comprising a plurality of ligands (L), each ligand comprising n ligand affinity domain regions (ADR), wherein n is at least two, wherein each ligand affinity domain region (ADR) has the ability of specific binding of at least one of the at least one substance, wherein one first ligand affinity domain region (ADR 1) is bound to the insoluble surface (IS) with a ligand to insoluble surface attachment region (SAR) and wherein ligand affinity domain region (ADR n) is bound to ligand affinity domain region (ADR n−1) with a ligand ADR joining region (AJR), wherein at least the ligand ADR joining region (AJR) comprises at least one selected from the group consisting of at least one charged group ($C_{AJR}$) and a noncharged link ($N_{AJR}$).

In one embodiment at least one of then ligand affinity domain regions (ADR) comprise a ligand solution terminal region (STR) comprising at least one charged group ($C_{STR}$).

In one embodiment the ligand to insoluble surface attachment region (SAR) comprises at least one charged group ($C_{SAR}$).

In one embodiment the ligand ADR joining region (AJR) comprises at least one charged group ($C_{AJR}$). In an alternative embodiment the ligand ADR joining region (AJR) comprises a noncharged link ($N_{AJR}$). It is conceived that the noncharged link ($N_{AJR}$) gives a space between the ADRs. Thus the noncharged link has suitably adapted length. In one embodiment the noncharged link ($N_{AJR}$) comprises 1-5 amino acids. Regarding the possible mechanism of the at least one charged group ($C_{AJR}$) it is described above. Regarding the possible mechanism of the noncharged link ($N_{AJR}$) it is unknown but the inventor speculates that it may be due to a larger spacing between the binding domains.

In one embodiment the at least two ligand affinity domain regions (ADR) are parts of one molecule selected from the group consisting of a protein, a polypeptide, and a polynucleotide. In one embodiment the at least two ligand affinity domain regions (ADR) are parts of one protein molecule. Herein an oligopeptide is encompassed in the term polypeptide and an oligonucleotide is encompassed in the term polynucleotide. If an oligopeptide comprises more than two amino acid residues it is considered to be encompassed by the term polypeptide. If an oligonucleotide comprises more than two nucleotides it is considered to be a polynucleotide. Aptamers are encompassed as ligands. In one embodiment the ligand is an aptemer. In one embodiment the at least two ligand affinity domain regions (ADR) are parts of one molecule selected from the group consisting of Protein A, Protein G, Protein NG, Protein L, and a derivative thereof. In one embodiment the at least two ligand affinity domain regions (ADR) are parts of one Protein A molecule or a derivative thereof.

In one embodiment the protein molecule has been modified to add at least one charged group $C_{AJR}$ to the at least one ligand ADR joining region (AJR).

In one embodiment the ligand is a protein and the protein comprises a polyhistidine tag. In one embodiment the polyhistidine tag is a His 6 tag. In one embodiment the ligand is a protein and the protein comprises a cysteine-polyhistidine tag. In one embodiment the cysteine-polyhistidine tag is a Cys-His 6 tag. The histidine tag facilitates purification and the Cys can facilitate subsequent coupling to a surface. The tags may be constructed so as to be cleavable under specific conditions. In one embodiment the polyhistidine tag is cleavable.

In one embodiment the at least one substance is an immunoglobulin or a derivative thereof. In one embodiment the at least one substance is an Fc linked therapeutic protein. In one embodiment the at least one substance in an antibody drug conjugate (ADC) or a polymer modified antibody or related protein.

In one embodiment the number n of ligand affinity domain regions (ADR) is from 2 to 10.

In one embodiment if present the at least one charge $C_{AJR}$ and if present also $C_{STR}$ and $C_{SAR}$ are negative charges. In an alternative embodiment if present the at least one charge $C_{AJR}$ and if present also $C_{STR}$ and $C_{SAR}$ are positive charges. If any charges are present, then they can be positive or negative.

In one embodiment each ligand ADR joining region (AJR) comprises 2-10 charged groups $C_{AJR}$. In one embodiment each ligand ADR joining region (AJR) comprises 3-7 charged groups $C_{AJR}$. In one embodiment each ligand ADR joining region (AJR) comprises at least 3 charged groups $C_{AJR}$. In one embodiment each ligand ADR joining region (AJR) comprises at least 5 charged groups $C_{AJR}$. In one embodiment each ligand ADR joining region (AJR) comprises at least 6 charged groups $C_{AJR}$. In one embodiment each ligand ADR joining region (AJR) comprises at least 7 charged groups $C_{AJR}$. In one embodiment each ligand ADR joining region (AJR) comprises at least 8 charged groups $C_{AJR}$. In one embodiment each ligand ADR joining region (AJR) comprises at least 9 charged groups $C_{AJR}$. In one embodiment each ligand ADR joining region (AJR) comprises at least 10 charged groups $C_{AJR}$.

In one embodiment the charged groups ($C_{AJR}$, $C_{STR}$, $C_{SAR}$) are parts of amino acid residues.

In one embodiment the adsorptive insoluble surface (IS) is a part of a sensor chip. In one embodiment the adsorptive insoluble surface (IS) is a part of a surface intended for an enzyme-linked immunosorbent assay (ELISA). In one embodiment the adsorptive insoluble surface (IS) is a part of the stationary phase in affinity chromatography. In one embodiment the adsorptive insoluble surface (IS) is a part of a chromatographic resin. In one embodiment the adsorptive insoluble surface (IS) is a part of a chromatographic monolith. In one embodiment the adsorptive insoluble surface (IS) is a part of a chromatographic fiber. In one embodiment the adsorptive insoluble surface (IS) is a part of a chromatographic filter. In one embodiment the chromatographic filter is adapted for plasmapheresis, i.e. it is intended to be used for plasmapheresis. In one embodiment the adsorptive insoluble surface (IS) is a responsive polymer.

In a second aspect there is provided a method of isolating at least one substance from a liquid comprising the steps of:
a) contacting the liquid comprising the at least one substance with the adsorptive insoluble surface (IS) as described above, under conditions where each ligand affinity domain region (ADR) has the ability of binding the at least one substance,
b) optionally washing the adsorptive surface,
d) eluating the at least one substance under conditions where each ligand affinity domain region (ADR) has reduced ability of binding the at least one substance.

In a third aspect there is provided a nucleic acid encoding a recombinant protein, said protein comprising n ligand affinity domain regions (ADR), wherein n is at least two, wherein each ligand affinity domain region (ADR) has the ability of specific binding of at least one of the at least one substance, wherein one first ligand affinity domain region (ADR 1) is bound to the insoluble surface (IS) with a ligand to insoluble surface attachment region (SAR) and wherein ligand affinity domain region (ADR n) is bound to ligand affinity domain region (ADR n–1) with a ligand ADR joining region (AJR), wherein at least the ligand ADR joining region (AJR) comprises at least one selected from the group consisting of at least one charged group ($C_{AJR}$) and a noncharged link ($N_{AJR}$).

In a fourth aspect there is provided a protein expression system comprising the nucleic acid as described above. The protein expression system is any known and suitable protein expressing system capable of expressing the desired protein for the present invention to be used as a ligand—one example of which is the *E. coli* expression system given in the Examples.

In a fifth aspect there is provided a method of manufacturing an adsorptive insoluble surface (IS) as described above, the method comprising binding a ligand to the surface using a ligand to insoluble surface attachment region (SAR). The ligand is attached to the surface using any known and suitable method. The examples show that the ligands can be terminally bound, e.g. via their 6-His N terminals, or randomly covalently bound (as to a CM-dextran SPR chip).

In one embodiment the method of manufacturing the adsorption insoluble surface comprises adding of charged groups by recombinant addition of charged amino acid residues, wherein the ligand is a protein.

In one embodiment the method of manufacturing the adsorption insoluble surface comprises alteration of existing amino acid residues so that they become the desired charge at the relevant pH, wherein the ligand is a protein.

In one embodiment the ligand is a protein expressed in a protein expression system as described above.

All the described alternative embodiments above or parts of an embodiment can be freely combined without departing from the inventive idea as long as the combination is not contradictory.

Other features and uses of the invention and their associated advantages will be evident to a person skilled in the art upon reading the description and the examples.

It is to be understood that this invention is not limited to the particular embodiments shown here. The embodiments and the following examples are provided for illustrative purposes and are not intended to limit the scope of the invention since the scope of the present invention is limited only by the appended claims and equivalents thereof.

EXAMPLES

Figure 6:
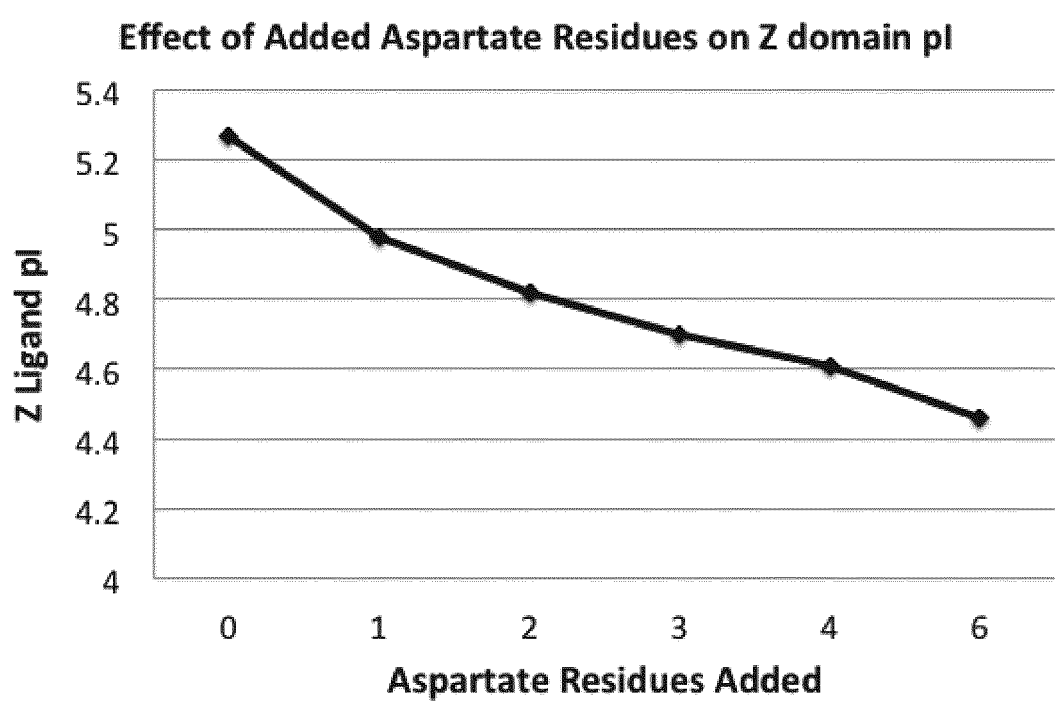
FIG. 6 shows simple Protcalc (protcalc.sourceforge.net) Z protein sequence charge versus pH modeling results, presented as pI versus one to six (N) added terminal end aspartate acid (D) residues. The direct inverse relationship between pI and N suggests addition of acid groups to affinity domain region (ADR) should have a strong effect on domain target binding effects. Similar results seen with glutamate residues. The Z sequence (1VDNKFNKEQQNAFYEILHLPNLNEEQR-NAFIQSLKDDPSQSANLLAEAKKL NDAQAPK 58) was taken from Yu, et al. and charge versus pH modeled using "protcalc.sourceforge.net" (Yu, F., Järver, P., Nygren, P-Å, Tailor-making a Protein A-derived domain for efficient site-specific photocoupling to Fc of mouse IgG1. PLoS ONE 8(2), 2013., e56597. doi:10.1371/journal.pone.0056597.
Figure 7:
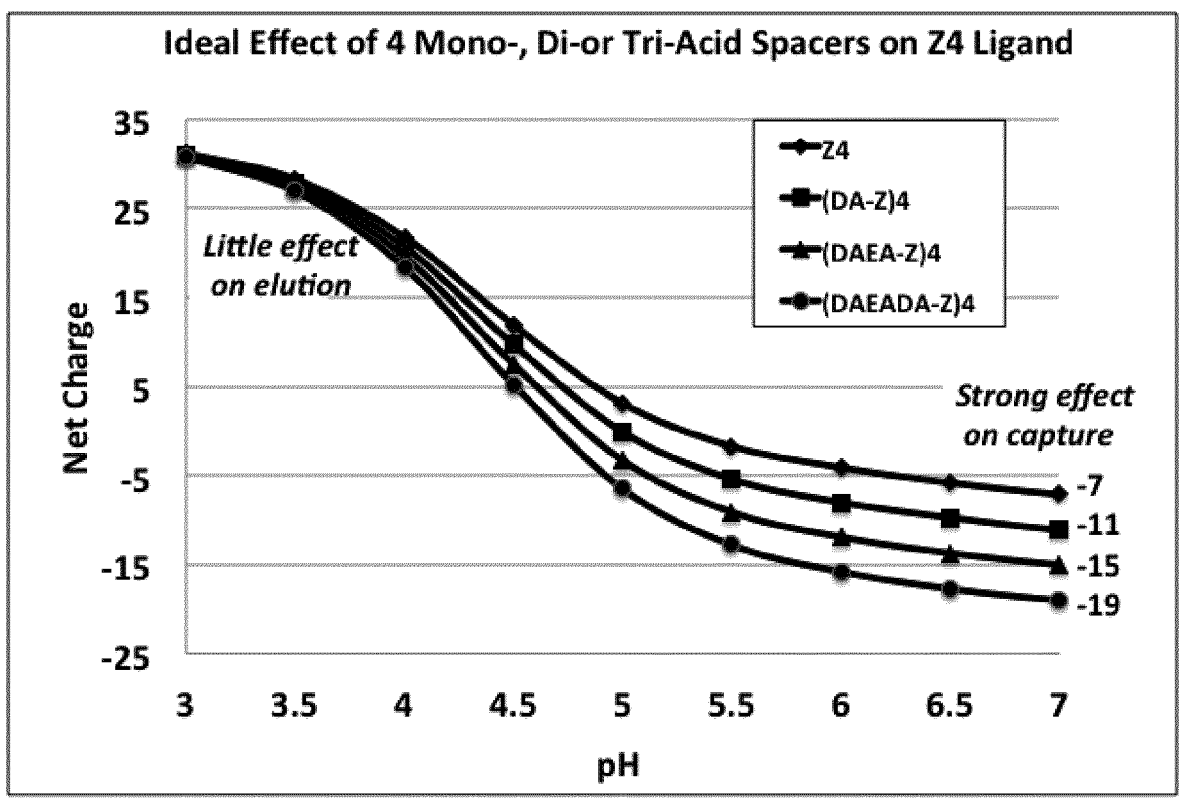
FIG. 7 shows simple Protcalc (protcalc.sourceforge.net) net charge versus pH modeling of tetravalent Z4 ligand modified with added charge residues in the structural regions linking its target binding ligand affinity domain regions (ADRs). Note that there is significant alteration in charge versus pH, commensurate with improved acidic buffering at binding pH 7, and perhaps some change in elution pH 4 but little alteration at elution pH 3. The enhanced charge at pH 7 may offer enhanced basic (pI>7) protein target localization and buffering capacity to offset local surface pH alteration caused by binding of basic protein targets.
Figure 8:
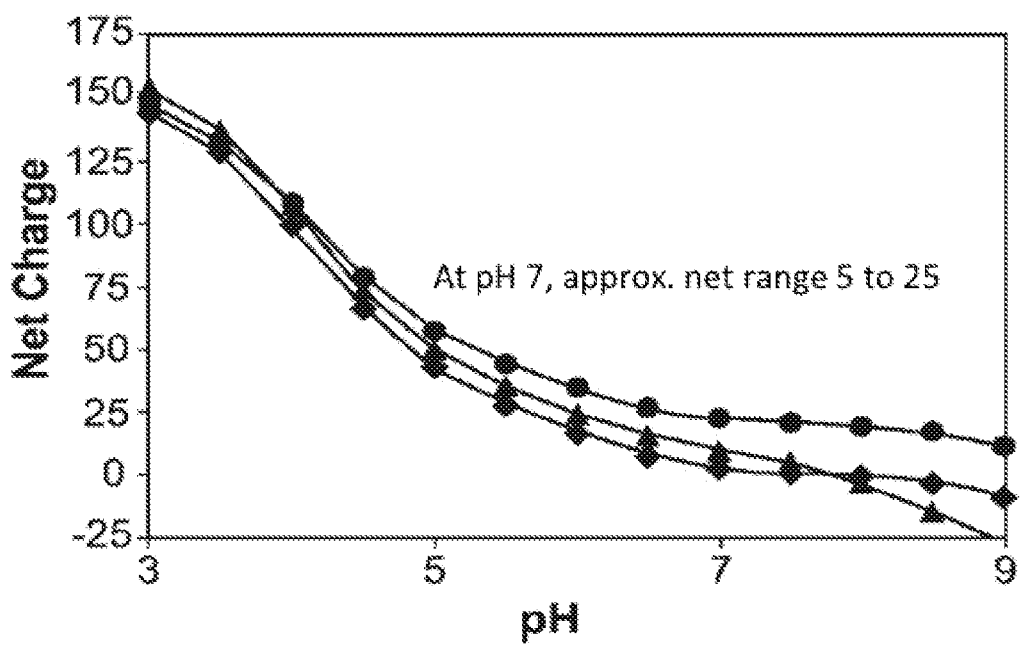
FIG. 8 shows net charge versus pH for three Genentech mAbs, which at pH 7 exhibit approximately +25 (mAb 1), +10 (mAb 2) and +5 (mAb3) charge. Figure from Harinarayan et al., 2006.
Figure 9:
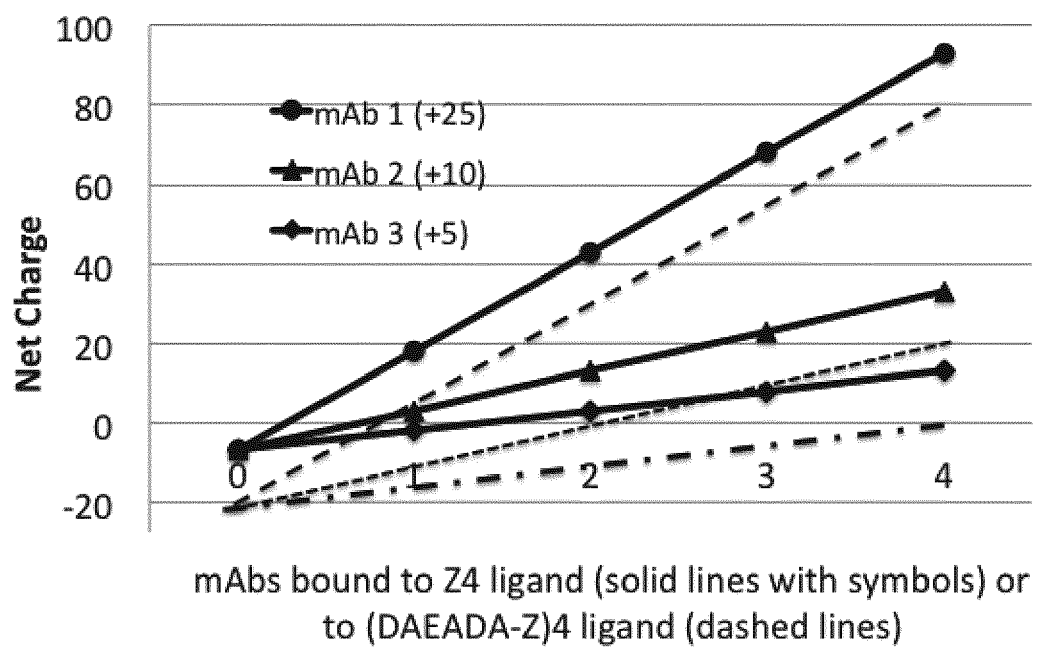
FIG. 9 shows simple Protcalc modeling of the net charge of Z4-mAb complexes as one to four mAbs of type 1, 2 or 3 from FIG. 8 are bound at pH 7. The mAbs dominate the charge nature of the complexes. The figure also shows reduction in the net charge of the complexes if the Z4 ligand contains three acidic residues separated by neutral alanine residues (DAEADA-Z)4.

Example 1. Simple Electrostatic Modelling of Protein Ligands and Ligand-mAb Complexes Introduction In order to gain insight into how a Protein A ligand binding domain (ADR) net charge would be affected by simple charge residue insertion in representative ADR joining regions the public domain internet (www) program Protcalc (protcalc.sourceforge.net) was used. For this modeling Z protein sequence charge versus pH modeling results, presented as pI versus one to six (N) added terminal end aspartate acid (D) residues. The Z sequence (1VDNKFNKEQQNAFYEILHLPNLNEEQR-NAFIQSLKDDPSQSANLLAEAKKL NDAQAPK) was taken from Yu, et al. and charge versus pH modeled using "protcalc.sourceforge.net" (Yu, F., Järver, P., Nygren, P-Å, Tailor-making a Protein A-derived domain for efficient site-specific photocoupling to Fc of mouse IgG1. PLoS ONE 8(2), 2013., e56597). The effect on pI of adding one to six aspartate or glutamate residues to the N terminal of one Z domain was calculated and plotted (FIG. 6). Next the effect of adding one, two or three aspartate (D) or glutamate (E9 residues interspersed with neutral alanine residues (A) on a tetrameric Z4 was calculated and plotted (FIG. 7). Then pH 7 net charge information related to three different Genentech mAbs (FIG. 8) was used to model the effect on net charge versus pH for a tetrameric Z4, or a tetrameric Z4 with AJR regions containing three added negative charge residues (two apartate and one glutamate interspersed with alanine residues) if binding one to four of each of the three different mAbs (FIG. 9).

Results and Discussion Single Z domain pI decreased linearly from 5.3 to 4.5 (approx. an order of magnitude) as 0 to six acidic residues were added. No significant difference was seen if aspartate versus glutamate residues were added or if the acidic residues were interspaced with neutral residues (not shown). These results suggest even adding in one or two acid residues may affect pI related charge properties of the domain. It was expected however than more charged groups (e.g. 3-6) might be required to show appreciable local region buffering effects. Significant expected effect of AJR modification with four mono-, di-, or tri-acid residues on pH versus net charge tetrameric Z4 model ligand (FIG. 7) was verified. A strong effect, which increased with acid residue addition, was seen at normal adsorption pH 7 with little effect at elution pH 3 when the acid residues were uncharged. At pH 7 the domains should offer enhanced buffering of local surface pH changes related to binding of basic mAb protein targets. Some differences were noted at pH 3-4.5 which may allow for favorably altered elution pH. Variation in the charge nature of mAbs was investigated using literature data from three Genentech mAbs which at pH 7 exhibited net positive charge from +25, +1+, and +5 (FIG. 8). Results suggest (FIG. 9) that native tetrameric Z4 ligand complexed with one to four mAbs should vary in net charge at pH 7 of from −5 to approximately +42, +12, +2 as only two mAbs were bound per ligand, respectively. Binding 4 mAbs would double the positive charge density suggesting a significant, nonsteric, barrier to additional mAb binding. Addition of even three charged residues per AJR was able to significantly reduce such effects.

Example 2. Cloning, Expression, Purification and Electrophoretic Analysis of Neutral and Charge Residue Enhanced Z4 Ligands Experimental: FIG. 10 details the sequences of two tetravalent (tetrameric) ligands (FIG. 5 schematics b and c) similar to the Z ligand structures noted in the above electrostatic charge modeling—augmented with N terminal 6-His and addition of either three aspartate acid residues (DDD), or three neutral residues formed by a mixture of glycine (G) or serine (S) residues, to AJR and STR regions.

Materials and Methods: The synthetic genes 4_Z_ASP and 4_Z_GGS were synthesized from commercial vendors (IDT, USA). The expression vector pET28b was obtained from Novagen. The 4_Z_GGS gene was digested with NdeI and XhoI restriction sites and was inserted into linearized pET28b vector. Similarly, the 4_Z_ASP gene was digested with NdeI and HindIII restriction sites and cloned into pET28b vector. Both the vectors were transformed into

*Escherichia coli* BL21 (DE3) cells. The "correctness" of the resulting pET28b-4_Z_ASP and pET28b-4_Z_GGS was confirmed by analytical digestion and DNA sequencing (GATC Biotech, Germany).

Expression of the Protein: 5 ml of LB medium (tryptone 10 g L-1, yeast extract 5 g L-1, NaCl 10 g L-1) supplemented with 50 µg/mL kanamycin was inoculated from a single bacterial colony and was incubated for overnight at 37° C. with shaking at 150 rpm. For the expression of the ligands, cells were grown in freshly prepared 200 ml LB media at 37° C. on a shaking incubator. The protein expression was induced by 0.2 mM Isopropyl β-D-1-thiogalactopyranoside (IPTG) when the OD600 reached 2.0. Further the cells were grown overnight and the temperature was reduced to 28° C. while the shaking was set 150 rpm.

Clarification and Purification: Cells were collected by centrifugation at 8000 rpm for 10 min. Cells were washed in 50 mM Tris-HCl buffer pH 7.5 containing 500 mM NaCl and 10 mM Imidazole. Disruption of the cells was carried out using Q-Sonica sonicator. Supernatant was collected using centrifugation at 10000 rpm for 15 min and passed through 0.45 µM filter. Filtered supernatant was loaded onto the 1 ml Hi-Trap Sepharose FF chelating column (GE Healthcare Biosciences, Uppsala) equilibrated with same buffer. Elution of the protein was achieved by running the gradient of the buffer containing 500 mM imidazole. Different fractions of the protein were collected and pooled together. Concentrated samples were passed through a PD-10 column (GE Healthcare Biosciences, Uppsala) to remove the imidazole. Samples were stored at 4° C. until further use.

Figure 12:
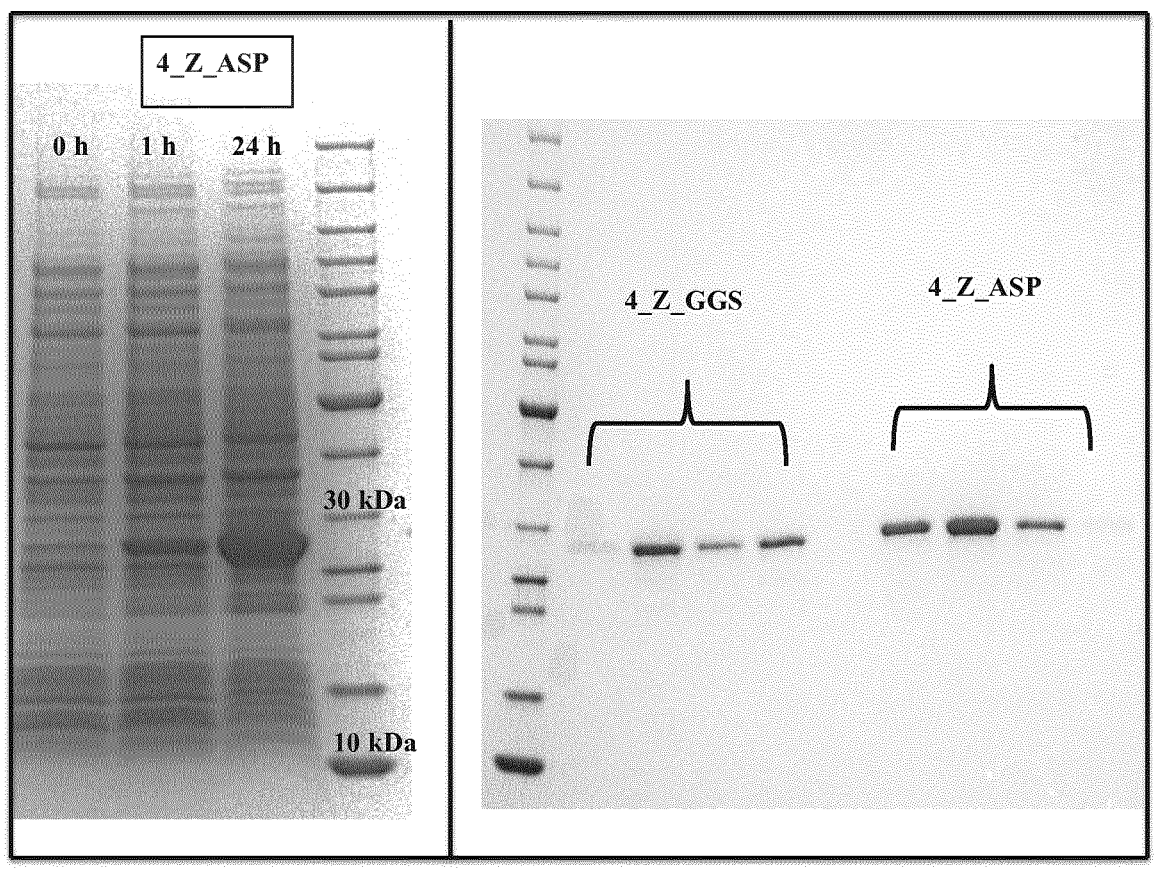
FIG. 12 shows expression of the 4_Z_ASP ligand protein and host cell proteins analyzed by SDS PAGE. Similar results were seen with the 4_Z_GSS ligand. On the right is shown the purity of the ligand fractions from IMAC chromatography, estimated to be approximately 95%.

Results: Both the genes were cloned and expressed successfully. Bacterial cells were collected after every hour of induction. It was found that the expression of the protein was observed after one hour of induction (FIG. 12.) However, the expression was continued overnight. The bacterial cells were collected after induction of the protein expression. The plasmid containing 4_Z_GGS was induced with 0.2 mM isopropyl β-D-1-thiogalactopyranoside (IPTG) and cells were collected at different time interval. Similarly, pET 28b vector without the gene insert was chosen for the study and showed sodium docecyl sulfate polyacrylamide gel electrophoresis (SDS PAGE) HCP expression results (not shown) similar to the 0 h results in FIG. 12. The prominent band at 26 kDa shows the protein was expressed after one hour of induction. The plasmid containing 4_Z_DDD was also analyzed after induction (FIG. 12). It was observed that the expression of the protein was significant after overnight cultivation of the cells.

Figure 11:
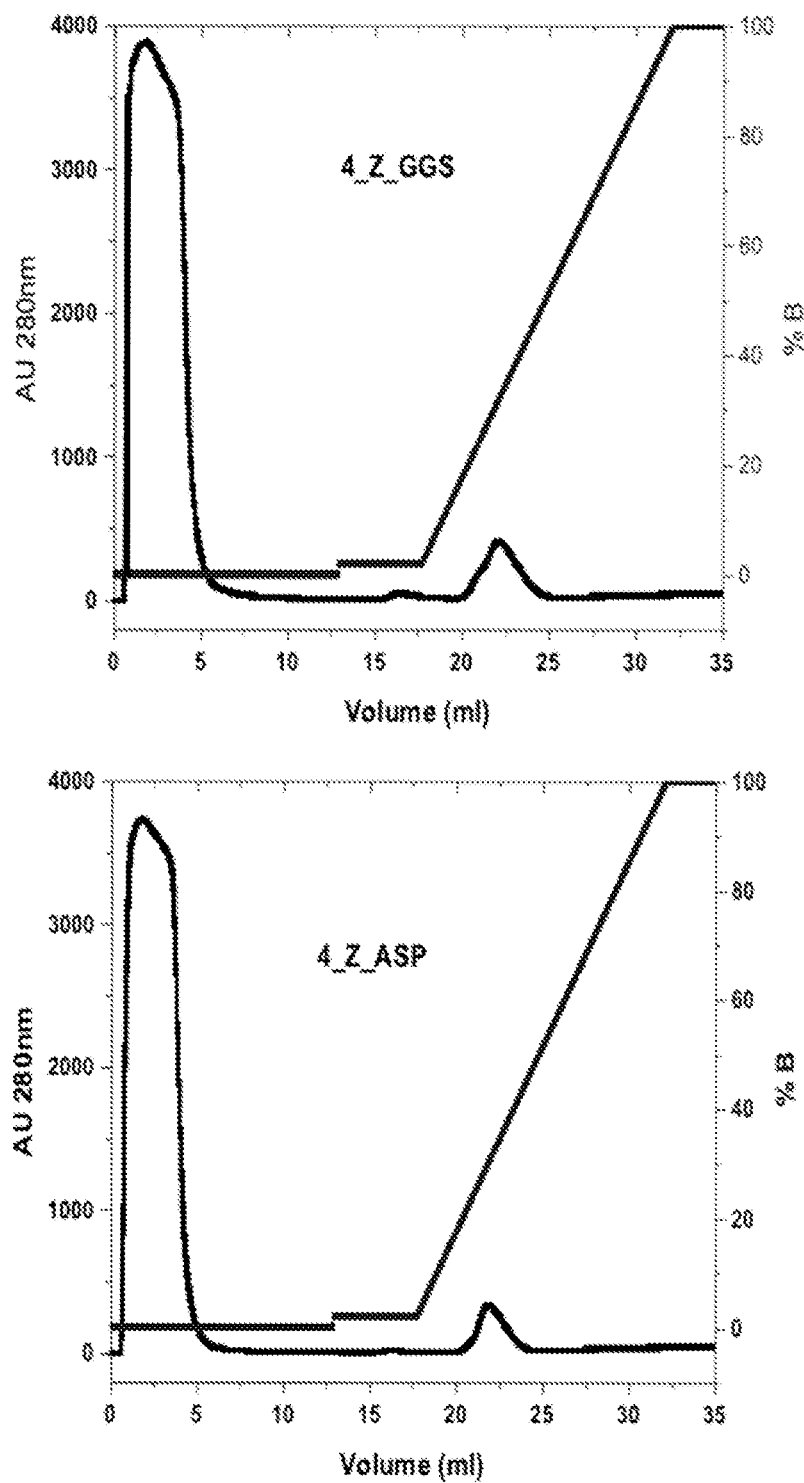
FIG. 11 shows the purification of the protein GSS and ASP ligands by Immobilized Metal Ion Affinity Chromatography (IMAC) facilitated by 6-Histidine tag at the N-terminal of the ligands. Samples were loaded onto a 1 ml IMAC column and were eluted by increasing the imidazole concentration. As shown, both the proteins showed similar chromatograms.

Protein Ligand Purification by IMAC and Anion Exchange: Purification of the ligand proteins were facilitated by Histidine tags at the N-terminal of the proteins. Samples were purified using a 1 ml Immobilised Metal Ion Chromatography (IMAC) column operated according to the manufacturer (see above). The proteins were eluted using a gradient of increasing imidazole concentration. As shown in FIG. 11, both ligand proteins showed similar chromatograms with good separation of HCP and target. Results of target fraction SDS PAGE analysis are shown in FIG. 12. The IMAC procedure appeared to yield ligand at approximately 95% purity. It was possible to purify approximately 4 mg of target in one chromatographic run on a 1 mL column. In a related study anion exchange (AEX) was used to purify the charge enhanced "ASP" ligand to good effect yielding similar but not better SDS PAGE results (not shown). Given the higher capacities and less costly buffers used for ion exchange chromatography compared to IMAC it may be a better approach for larger scale purification of such ligands.

Discussion: The ligands were readily cloned, expressed at high concentrations, recovered, and affinity purified using the methods noted above. Obviously other methods would be possible particularly in regard to ligand purification by chromatography.

Example 3—Determination of Binding Affinities at pH 7

Introduction: Surface Plasmon Resonance (SPR) is a method of choice for determination of binding constants and is favored in ligand evaluation as it provides a "label-free" and relatively unhindered "mass transport independent" data set. If allowing for mass transport effects there is good correlation between the kinetic binding and release results obtained with SPR and affinity chromatography results (Zheng, X., Bi, C., Li, Z., Podariu, M., and Hage, D. S., Analytical methods for kinetic studies of biological interactions: A review, Pharm Biomed Anal. 2015 Sep. 10; 113: 163-180). In SPR one interaction partner (ligand or target) is immobilized on an SPR chip surface and the complementary interaction partner is exposed to the surface at various concentrations in a buffer of known pH, conductivity, composition etc. After plateau adsorption is reached buffer without target is flowed over the chip and desorption is monitored. It is easy to recover three key types of data for different concentrations—a Ka association constant, a Kd dissociation constant and a relative Response Unit (RU). RU values correspond to approximate protein surface concentrations of one picogram per square millimeter on carboxymethyl CM5 SPR Chip (GE Healthcare, Biacore Assay Handbook, Biacore Assay Handbook 29-0194-00 Edition AA, GE Healthcare, 2012) and relatively comparable on the same chip under the same conditions. SPR devices normally come with data fitting software and in some cases, such as those involving multi-dentate ligands, it is better to fit Ka and Kd values using a multivalent fit such as the "bivalent fit" used in the present studies. This gives two sets of rate constants (Ka1, Ka2, Kd1, Kd2) with the second set being related to more complicated interpretation. In the present comparative study we focus on Ka1 and Kd1 and have used them to calculate common $K_D$ values ($K_D$ is the equilibrium dissociation constant, a ratio of kd/ka, between the antibody and its antigen such that $K_D$ and affinity are inversely related—in some literature papers $K_D$ is written Kd). In the present study plasma extracted polyclonal human IgG (GammaNorm) was used so the results relate to a broad range of IgG types, in addition it allowed for relatively dense loading of IgG onto the ligand modified surfaces so that the data was more in keeping with chromatographic results. So too, the CM5 carboxymethyldextran coated chip surface is analogous to the surfaces of various chromatography resins.

Experimental: Unless noted all reagents were obtained from Sigma Aldrich. The SPR studies were performed in a contract laboratory facility at the University of Lund, Lund, Sweden and undertaken by professionals with extensive experience in performing and analyzing the results of such work.

1. Capture of IgG by SPR Chip Bound Ligands: Initial SPR experiments involved 95% pure (IMAC purified) 6HIS-Z4 ligands modified with neutral (control) or charged residues in the antibody binding domain joining regions (AJRs) and free solution terminal region (STR). The neutral control AJRs and STR had three neutral charged amino acid residues chosen from glycine, and serine (i.e. GSS, GGS . . . ) while the charge ligand had three aspartic acid (DDD) residues. Binding characteristics between "4_Z_GGS" (29666.63 Da) or "4_Z_ASP" (30182.91 Da) and normal human immunoglobulin were carried out using a BIAcore X-100 instrument (GE Healthcare, Uppsala, Sweden). 4_Z_GGS and 4_Z_ASP were randomly immobilized via their free amine groups on different CM5 sensor chips (GE Healthcare) by standard amine coupling in 10 mM acetate buffer pH 5.0. In parallel, one flow cell was incubated with buffer alone to serving as control.

4_Z_GGS was immobilized at a density of 486.4 final response units (RUs) on the flow cell 2 of CM5 chip (GE Healthcare) whereas 4_Z_ASP was immobilized at a density of 572.4 RUs. Interaction experiments were performed with injections of 31.25, 62.5, 125, 250, 500, and 1000 nM of normal human polyclonal immunoglobulin G (GammaNorm, Octapharma) in running buffer HBS-EP (10 mM HEPES pH 7.4, 150 mM NaCl, 3.4 mM EDTA, 0.005% surfactant P20) for 120 seconds and allowed to dissociate for 600 seconds at a flow rate of 30 μl/min. The sensor chip surface was regenerated with glycine HCl pH 1.5 for 60 seconds with a stabilization period of 15 seconds. After X and Y normalization of data, the blank curves from the control flow cell of each injected concentration were subtracted. The BIA evaluation 3.1 analysis software (GE Healthcare) was used to determine association and dissociation constants from the processed data sets by fitting to a Bivalent analyte molecular binding model.

Experimental Results: The results were typical for measurement of such interactions, and provided results in keeping with value ranges expected from the literature. In particular the analytical software gave an excellent fit to all concentration varied target ranges (see dotted lines in FIG. 13).

TABLE 4

Summary of SPR Results Related to IgG Binding to Ligands at pH 7

| Ligand* | On CM5 (RU) | RU (120 sec) | RUmax (calc.) | Kd1 (1/s) | Ka1 (1/Ms) | $K_D$ (nM)* |
|---|---|---|---|---|---|---|
| Protein A | NA | NA | NA | NA | NA | 7 |
| Z monomer | NA | NA | NA | NA | NA | 10 |
| SuRe Z4 | NA | NA | NA | NA | NA | 3-20 |
| (GGS-Z)4 | 486.4 | 1750 | 1926 | 2.82E-4 | 6.94E+4 | 4.1 |
| (DDD-Z)4 | 572.4 | 3300 (+60%) | 4477 (+100%) | 3.12E-4 | 5.74E+4 | 5.4 |

*$K_D$ = Kd/Ka and is the inverse of affinity. Protein A $K_D$ for IgG from Chloe et al., 2016. Z $K_D$ for Human IgG1 from Braisted and Wells,1996. SuRe (Z4) ligand $K_D$ for Fc fusion protein Etanercept and human IgG subclasses (except IgG3) from Nohldén, 2008. GSS and DDD (i.e. ASP) ligand results for polyclonal human IgG from the present study.
NA = not applicable.

Relative Amount of Target IgG Bound: The CM5 chip localization of the SSG and ASP ligands has an ASP/SSG RU value ratio of 1.18 which allowing for ligand mass suggests a ligand density ratio of 1.16. However at 1000 nM (i.e., 0.15 g/L) IgG the GGS ligand reached approximately 1750 RU's in 120 sec. The ASP (DDD) ligand reached 3300 in 120 sec. If we normalize for ligand density the observed (see Figure) ASP/GSS RU ratio is 1.62 equivalent to a 60% increase in what might be described as "dynamic surface capacity" for target IgG in the charge modified ligand. The calculated RUmax values based on the data sets suggests RUmax for GSS was 1926 and for ASP was 4477 (or 3869 based on ligand density). This suggests a calculated ASP/GSS RU ratio of 2.00 equivalent to a 100% increase in max dynamic surface capacity for target IgG in the charge modified ligand. Note that these significant capacity increases were for similarly sized ligands, at similar surface grafting densities, and as noted below are not related to differences in binding affinities.

Figure 13:
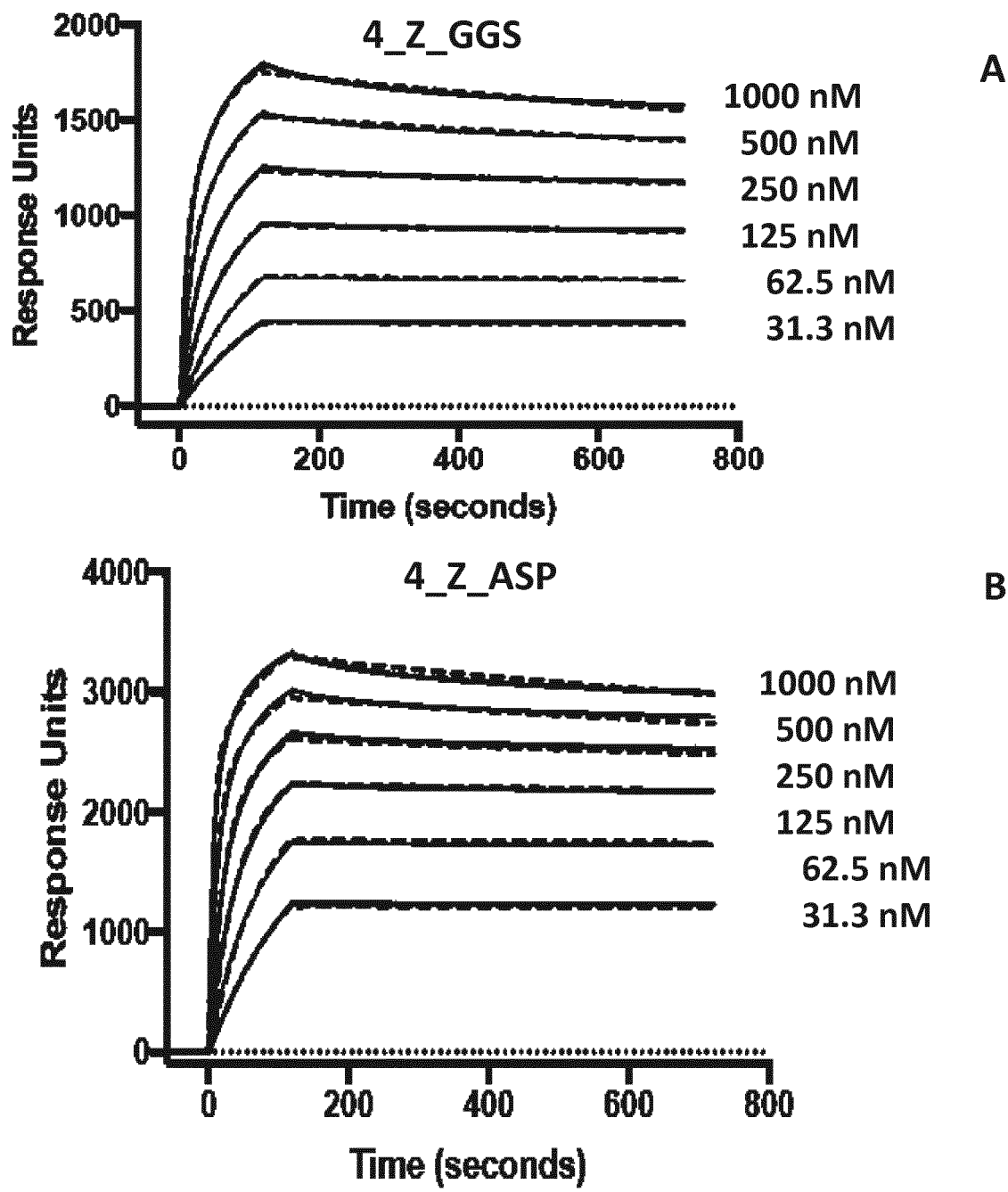
FIG. 13 shows Surface Plasmon Resonance kinetic and adsorption capacity data for human polyclonal IgG adsorbing to the GSS or ASP ligands covalently immobilized at approximately similar surface densities on carboxymethylcellulose dextran coated Biacore CM5 SPR chips. Both ligands exhibited nM affinity, with the charge residue modified ASP ligand exhibiting approximately double the capacity of the neutral residue modified GSS ligand.

Kinetic Results: As indicated in FIG. 13 and noted in the above table the "on and off" rates for the GSS and DDD ligand were quite similar, as were the calculated $K_D$ values, which appear within the range of expected $K_D$ for Protein A related binding domains such as Z (Table 3 and Discussion).

Discussion: SPR on CM5 (carboxymethyl) chip is perhaps the most established method of SPR. Andrew C. Braisted and James A. Wells of Genentech (Proc. Natl. Acad. Sci. USA, Vol. 93, pp. 5688-5692, June 1996 Minimizing a binding domain from protein A) gave the SPR determined dissociation constant ($K_D$) for Z (triple helix, 59 residues, IgG1 target) as 10 nM determined by adsorption of ligand onto an IgG coated SPR slide. They used amine coupling to the surface as was done in the present experiments. $K_D$ of Z4 for various human IgG subclasses (except IgG3 that does not bind) and an Fc Fusion protein was estimated to line in the range of 4 to 20 nM (Nohldén, S., Affinity Determination of Protein A Domains to IgG, Masters Thesis, LiTH-IFM-EX-08/1921-SE, Dept. of Physics, Chem. and Biology, Linkoping University, 2008). Braisted and Wells used phage display based large mutant library screening to develop a double helix version of Z (33 residues with KD 1000 nM). The significantly lower affinity was attributed to reduced ligand stability (enhanced mobility) though some loss of structure could also have contributed. After mutations in 12 residues to increase alpha-helicity based stability, a double helix Z variant exhibited a $K_D$ of 43 nM.

In a recent literature review Choe et al., noted that Protein A wild type (consisting of five different domains) has been reported to exhibit a Ka of 1.4×108 M-1, whose inverse suggests a domain average $K_D$ of 7.1 nM. (Choe, W., Trishaladevi, A. D., Chung, S. J., Materials 9: 994, 2016).

The charge and non-charge ligand enhanced versions of Z were able to strongly bind polyclonal Human IgG with $K_D$ values similar or slightly lower than literature Z values. The latter may be due simply to increasing the distance between binding domains. However it is noteworthy that the non-charge modified GSS ligand appears to also be a viable ligand candidate. Although it may not have the same capacity as the charge modified ligand such as ASP it may offer other advantages in regard to reduction of fouling under some processing conditions.

The charge and non-charge ligand affinities suggest native Z structure and high affinity antibody binding was maintained. Inclusion of 6HIS terminal in the ligands did not affect their ability to function. This has important implications as regards potential production of IgG ligands with 6HIS or other (e.g. GSH) tags which might aid their purification and use. (The fact the present novel ligands could be cloned and produced with 6 HIS tags is noteworthy. SDS PAGE Electrophoresis suggests the ligands could be purified to approximately >90% purity following one IMAC Chromatography step (see above). The IMAC and charge modified ligands would also be expected to be more readily purified if using ion exchange (Ref. Becker, K., Van Alstine, J., Bülow, L., Multipurpose peptide tags for protein isolation, Journal of Chromatography A, 1202: 40-46, 2008).

In spite of the charge and non-charge enhanced ligands exhibiting similar binding affinities the plateau amount in terms of RU units expected to reflect binding of target IgG per defined surface area was >60% higher at 120 s and 100% at calculated plateau saturation (Rmax). Historically even a 20% increase in dynamic binding capacity may commercial development of a new product (e.g. GE Healthcare MabSelect SuRe™ LX compared to PrismA™) Especially if it can be accomplished using similar molar amounts of ligands and binding domains.

The simplest explanation for the doubling of RU is that while the Z domains of the charge and non-charge modified ligands were similar, as were their affinity constants, more of the domains in the charge modified ligand were able to participate in target binding. The tetravalent/tetrameric Z based MabSelect™ SuRe ligand is often referred to binding an average of 1 to 1.5 IgGs per ligand. If the noncharge modified variant studied here reflects similar stoichiometry, or possibly 1 to 2, then the charge modified variant would appear to bind 2 to 4 IgGs per tetravalent ligand. To our knowledge such effective utilization of tetravalent Protein A based ligand capacity has not been reported earlier. If the doubling seen in SPR analysis could translate to even a 50% increase in chromatographic dynamic capacity it could reduce resin costs by a similar factor, and also allow reductions in columns sizes, buffer volumes, processing times, etc.

Such potentially dramatic increases in ligand density, especially at shorter residence times could also affect choice of processing methods (large batch columns versus smaller continuously operated columns. Similar considerations would function in regard to operations involving monoliths, filters, ELISA plates, sensor chips, etc.

We assume the adsorbed IgG was polyclonal in nature but did not contain IgG3 as commercial Protein A resins typically cannot bind IgG3. However the latter assumption may not be valid and charge enhanced protein affinity ligands may be able to bind IgG3, as well as other "low dynamic capacity" targets such as Fc-Fusion Proteins, ADC's, and polymer modified mAbs and Fabs.

2. Capture of Z4 Ligand Mutants by SPR Chip Bound IgG: The above SPR experiments more closely resemble the realities of IgGs being bound by ligands on a surface—although in the present study the ligands were randomly, not terminally, tethered to the surface. As a control the same experiments were run with ligand adsorbing to IgGs covalently immobilized on CM5 chips.

Binding characteristics between 4_Z_GGS (29666.63 Da) or 4_Z_ASP (30182.91 Da) and normal human immunoglobulin were carried out using a BIAcore X-100 instrument (GE Healthcare, Uppsala, Sweden). Normal human immunoglobulin was immobilized on CM5 sensor chips (GE Healthcare) by standard amine coupling in 10 mM Acetate buffer pH 5.5. In parallel, one flow cell was incubated with buffer alone serving as a control. Normal human immunoglobulin was immobilized at a density of 699.2 final response units (RUs) on the flow cell 2 of CM5 chip. Interaction experiments were performed with injections of 31.25, 62.5, 125, 250, 500, and 1000 nM of 4_Z_GGS and 4_Z_ASP in running buffer HBS-EP (10 mM HEPES pH 7.4, 150 mM NaCl, 3.4 mM EDTA, 0.005% surfactant P20) for 120 seconds and allowed to dissociate for 600 seconds at a flow rate of 30 µl/min. The sensor chip surface is regenerated with Glycine HCl pH 1.5 for 60 seconds. After X and Y normalization of data, the blank curves from the control flow cell of each injected concentration were subtracted. The BIA evaluation 3.1 analysis software (GE Healthcare) was used to determine association and dissociation constants from the processed data sets by fitting to a Bivalent analyte molecular binding model with drift.

TABLE 5

Summary of SPR Results Related to IgG Binding to Ligands at pH 7

| Ligand* | IgG CM5 (RU) | RU (1 mM) (120 sec) | RUmax (calc.) | Kd1 (1/s) | Ka1 (1/Ms) | $K_D$ (nM)* |
|---|---|---|---|---|---|---|
| (GGS-Z)4 | 699 | 30 | 23.5 | 2.36E−3 | 1.27E+6 | 1.9 |
| (DDD-Z)4 "ASP" | 699 | 33 | 40.5 (+100%) | 1.27E−2 | 1.23E+5 | 103 |

*Equivalent conditions were used and it is assumed based on previous results that the density of IgG on the surfaces were comparable.

Figure 14:
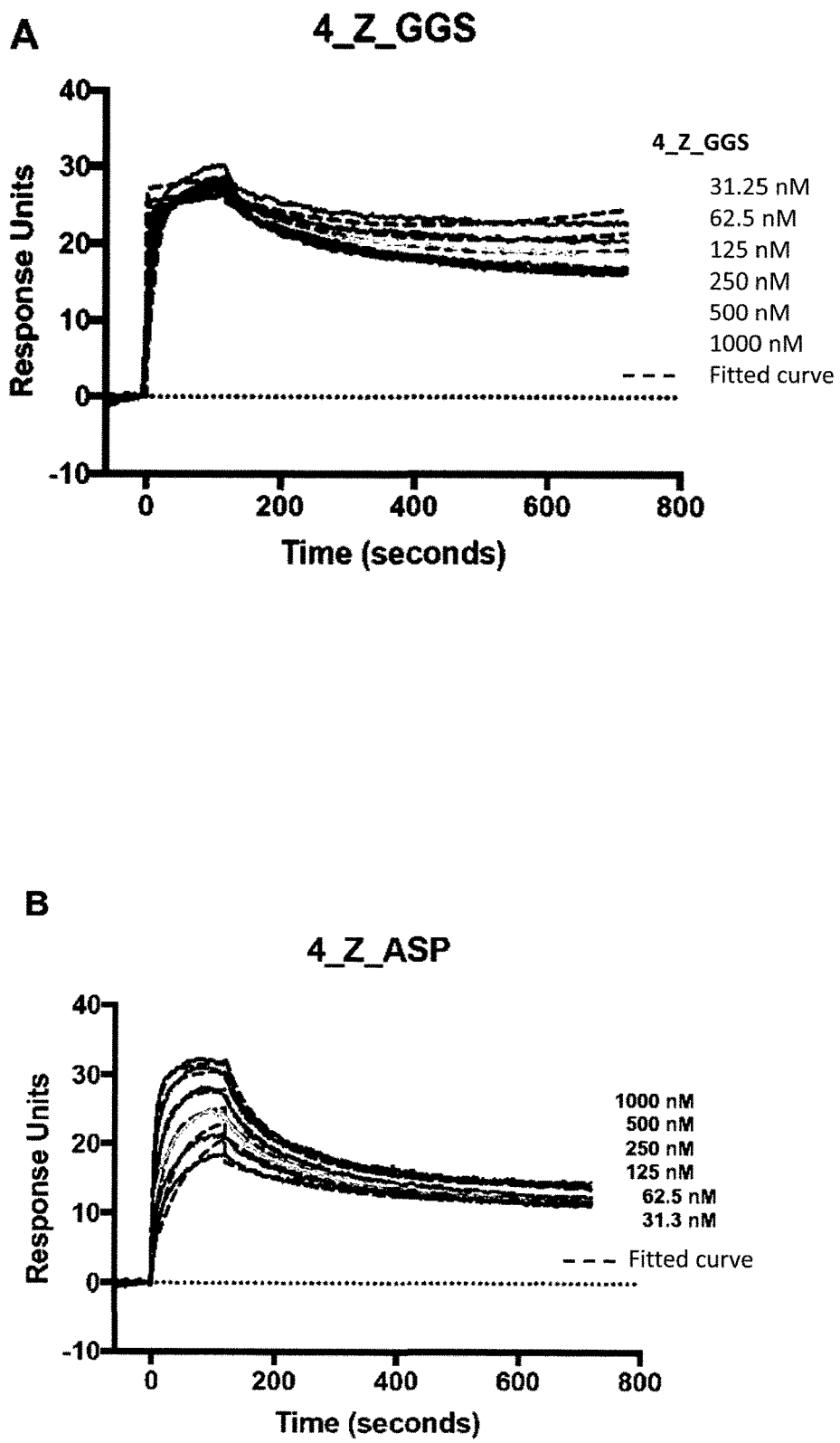
FIG. 14 shows Surface Plasmon Resonance kinetic and adsorption capacity data for the charge modified ASP ligand and the neutral residue modified GSS adsorbing onto a CM5 chip covalently coated with human polyclonal IgG. This set of experiments is a control on that in FIG. 13 and indicated that the ligands exhibit good affinity and the ASP ligand offered double capacity (RUmax) with some ligand differences related to their recombinant modifications.

Results and Discussion: In this study relatively small ligands must interact with the surface coated with IgG and diffuse in a manner so as to find the Fc site for their affinity interaction. The neutral residue enhanced GSS ligands showed high affinity with KD of approximately 2 nM which is slightly greater affinity than for the complementary "ligand binding to surface immobilized IgG study" noted above. Interestingly the charge enhanced "ASP" ligand apparently exhibited a 20 fold reduction in affinity ($K_D$ 20 to 100 nM). The reasons for this are unknown but it may be due to the net positive nature of the surface bound IgG and the net negative nature of the ligand contributing, even at relatively high conductivity, to reducing ligand diffusion in the vicinity of the IgG. Importantly differences were seen in the ligands, and in spite of reduced affinity the calculated RUmax values for the charge enhanced ligands were, once again, double that of the neutral residue enhanced ligands. Differences in the ligands are also evident from the SPR graphs in FIG. 14.

Low pH elution studies were not possible with the CM5 chip model as the antibodies tend to bind nonspecifically to the chip at low pH.

Example 4. Chromatographic Verification of Ligand Capture and Elution of IgG

Figure 15:
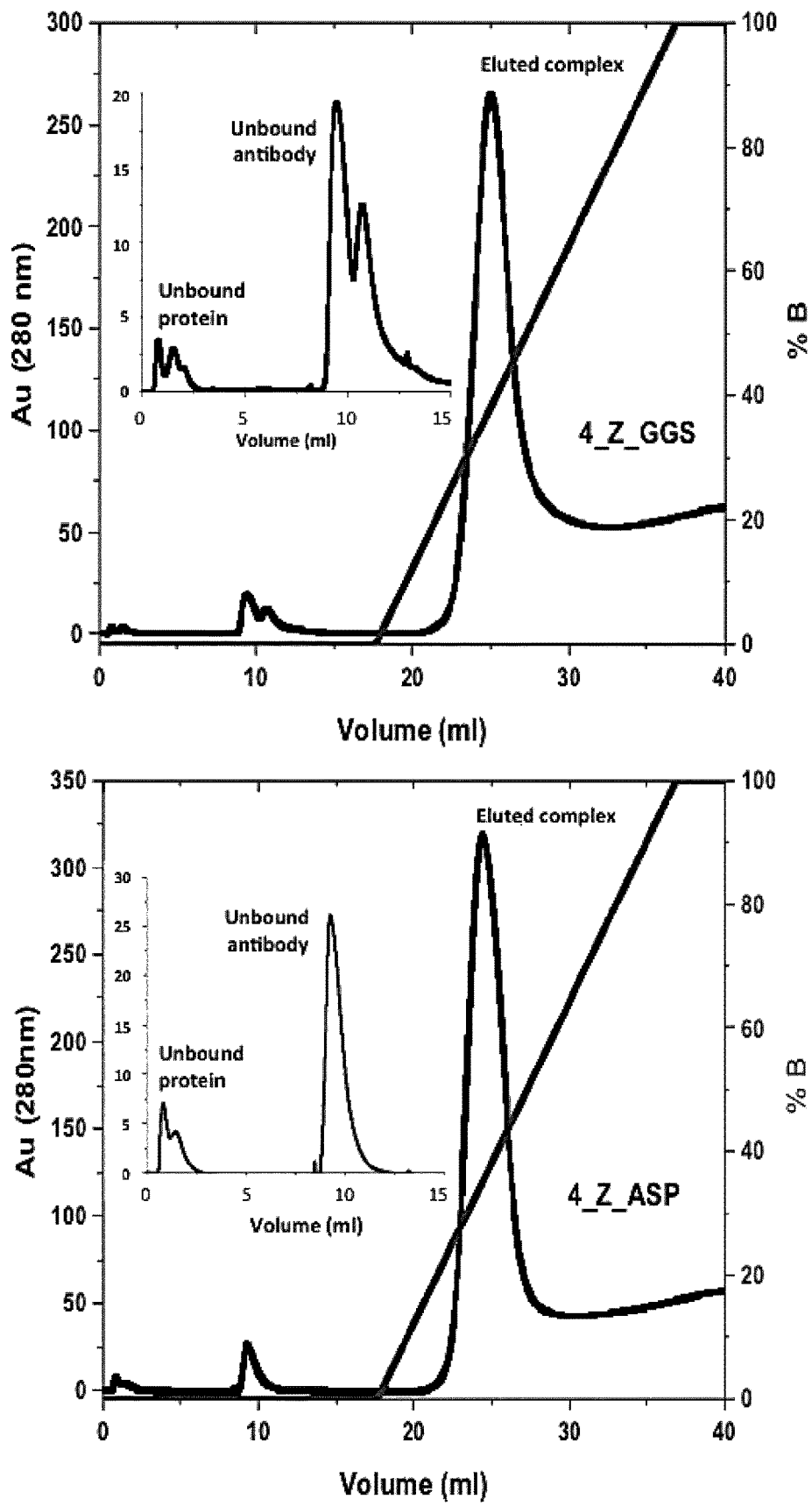
FIG. 15 shows the GSS and ASP ligands immobilized on IMAC column prior to exposure to polyclonal human IgG, in the presence of imidazole to reduce nonspecific IMAC interaction of the column with IgG histidine groups, In both cases the IgG is affinity captured by the ligands at pH 7, and is then eluted (as a ligand-IgG complex) in an imidazole gradient. The chromatograms clearly show IgG capture by the ligand.
Figure 16:
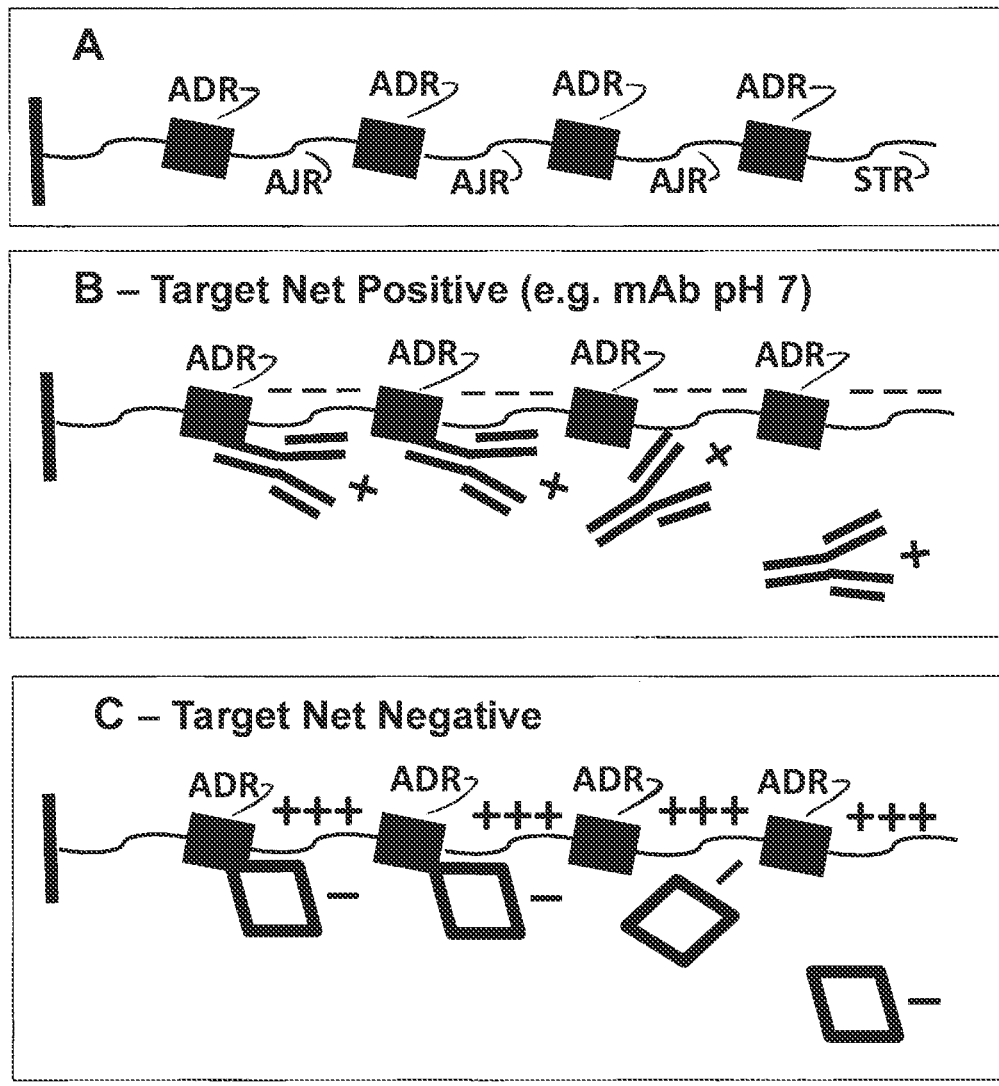
FIG. 16 shows a schematic of general concepts showing: (A) Tetravalent ligand which is composed or target affinity binding domain (ADR)s jointed by AJR regions and having an optional solution terminal region (STR). (B) Modification of the AJR and STR regions with negatively charged groups to enhance binding of a target which is net positive under binding conditions. (C) Modification of the AJR and STR regions with positively charged groups to enhance binding of a target which is net negative target under binding conditions. The ADR, AJR, or STR regions can be oligo- or poly-peptides but do not have to be, They could represent oligo- or poly-nucleotide structures or even organic chemical structures. The ligand can be multivalent.

The 6-His tags on the neutral GSS and charge enhanced ASP ligands allows for a simple test of the chromatographic potential. In commercial operation the ligands would be surface localized at high density via covalent linkage at a terminal end. In this experiment the ligands were localized via their 6 His tags to 1 mL IMAC columns in a manner similar to their purification. However following their column adsorption IgG containing solution was run through the column to allow IgG to potentially bind to the modified Z4 ligands. Protein ligands (0.5 mg/ml) were loaded onto the 1 mL column in 10 mM Tris HCl-pH 7.5 containing 500 mM NaCl and 10 mM imidazole. IgG in the same buffer at 5 mg/ml were loaded onto the column with residence time more than 6 min. Imidazole was used in the antibody loading buffer to reduce any nonspecific binding of IgG via its naturally occurring histidine residues. Elution of ligand-IgG complex was performed using a gradient of up to 500 mM imidazole. Results are shown in FIG. 15. We did not use a low pH 3 or 4 elution as the low pH can affect the IMAC column and IMAC affinity interaction making interpretation of results difficult.

As noted in FIG. 15 both of the modified ligands (GSS and ASP) were able to effectively bind IgG with gradient elution yielding reasonably sharp peaks. Assuming an average IgG MW of 155 KDa and ligand MW of 30 KDa (see above) the approximately 17 micromoles of potentially tetravalent ligand (with a total theoretical capacity of binding 68 micromoles of IgG) was exposed to the column in order to bind 22 micromoles of IgG. Under these conditions one would expect to see good target binding but neither ligand type capacity challenged, as in the SPR experiments. That would require exposure to perhaps twice the amount of IgG for the GSS ligand and perhaps four times the amount of IgG for the ASP (DDD) ligand.

The invention claimed is:

1. An adsorptive insoluble surface (IS) for binding at least one substance, said insoluble surface (IS) comprising a plurality of ligands (L), each ligand comprising n ligand affinity domain regions (ADR), wherein n is at least two, wherein each ligand affinity domain region (ADR) comprises a binding region of a protein selected from the group consisting of protein A, protein G, protein A/G, protein L, and derivatives thereof, and has the ability of specific binding of at least one of the at least one substance, wherein one first ligand affinity domain region (ADR 1) is bound to the insoluble surface (IS) with a surface attachment region (SAR) and wherein each ligand affinity domain region is bound to an adjacent ligand affinity domain region with a ligand ADR joining region (AJR), wherein each ligand ADR joining region (AJR) comprises at least three charged groups ($C_{AJR}$) added between adjacent ADRs, wherein each charged group $C_{AJR}$ comprises a charged amino acid residue selected from glutamic acid and aspartic acid, and wherein the charged groups modify a net charge the ligand would have in the absence of the added charged groups.

2. The adsorptive insoluble surface (IS) according to claim 1, wherein at least one of the n ligand affinity domain regions (ADR) comprises a ligand solution terminal region (STR) comprising at least one charged group ($C_{STR}$).

3. The adsorptive insoluble surface (IS) according to claim 1, wherein the surface attachment region (SAR) comprises at least one charged group ($C_{SAR}$).

4. The adsorptive insoluble surface (IS) according to claim 1, wherein the at least two ligand affinity domain regions (ADR) are parts of one protein molecule.

5. The adsorptive insoluble surface (IS) according to claim 1, wherein the at least two ligand affinity domain regions (ADR) are parts of one protein A molecule or a derivative thereof.

6. The adsorptive insoluble surface (IS) according to claim 1, wherein the ligand comprises a polyhistidine tag.

7. The adsorptive insoluble surface (IS) according to claim 1, wherein the ligand comprises a cysteine-containing polyhistidine tag.

8. The adsorptive insoluble surface (IS) according to claim 6, wherein the polyhistidine tag is cleavable.

9. The adsorptive insoluble surface (IS) according to claim 1, wherein the at least one substance is an immunoglobulin or a derivative thereof.

10. The adsorptive insoluble surface (IS) according to claim 1, wherein the at least one substance is an Fc linked therapeutic protein.

11. The adsorptive insoluble surface (IS) according to claim 1, wherein the at least one substance is an antibody drug conjugate.

12. The adsorptive insoluble surface (IS) according to claim 1, wherein the number n of ligand affinity domain regions (ADR) is from 2 to 10.

13. The adsorptive insoluble surface (IS) according to claim 1, wherein each ligand ADR joining region (AJR) comprises 3-10 charged groups $C_{AJR}$.

14. The adsorptive insoluble surface (IS) according to claim 1, wherein each ligand ADR joining region (AJR) comprises 3-7 charged groups $C_{AJR}$.

15. The adsorptive insoluble surface (IS) according to claim 1, wherein each ligand ADR joining region (AJR) comprises at least 5 charged groups $C_{AJR}$.

16. The adsorptive insoluble surface (IS) according to claim 1, wherein each ligand ADR joining region (AJR) comprises at least 6 charged groups $C_{AJR}$.

17. The adsorptive insoluble surface (IS) according to claim 1, wherein each ligand ADR joining region (AJR) comprises at least 7 charged groups $C_{AJR}$.

18. The adsorptive insoluble surface (IS) according to claim 1, wherein each ligand ADR joining region (AJR) comprises at least 8 charged groups $C_{AJR}$.

19. The adsorptive insoluble surface (IS) according to claim 1, wherein each ligand ADR joining region (AJR) comprises at least 9 charged groups $C_{AJR}$.

20. The adsorptive insoluble surface (IS) according to claim 1, wherein the adsorptive insoluble surface (IS) is a part of a sensor chip.

21. The adsorptive insoluble surface (IS) according to claim 1, wherein the adsorptive insoluble surface (IS) is a part of a surface intended for an enzyme-linked immunosorbent assay (ELISA).

22. The adsorptive insoluble surface (IS) according to claim 1, wherein the adsorptive insoluble surface (IS) is a part of the stationary phase in affinity chromatography.

23. The adsorptive insoluble surface (IS) according to claim 1, wherein the adsorptive insoluble surface (IS) is a part of a chromatographic resin.

24. The adsorptive insoluble surface (IS) according to claim 1, wherein the adsorptive insoluble surface (IS) is a part of a chromatographic monolith.

25. The adsorptive insoluble surface (IS) according to claim 1, wherein the adsorptive insoluble surface (IS) is a part of a chromatographic fiber.

26. The adsorptive insoluble surface (IS) according to claim 1, wherein the adsorptive insoluble surface (IS) is a part of an affinity filter.

27. The adsorptive insoluble surface (IS) according to claim 26, wherein the filter is a chromatographic filter and is adapted for plasmapheresis.

28. The adsorptive insoluble surface (IS) according to claim 1, wherein the adsorptive insoluble surface (IS) is a responsive polymer.

29. The adsorptive insoluble surface (IS) according to claim 2, wherein the at least one charged group $C_{STR}$ has a negative charge.

30. The adsorptive insoluble surface (IS) according to claim 2, wherein the at least one charged group $C_{STR}$ has a positive charge.

31. The adsorptive insoluble surface (IS) according to claim 2, wherein each charged group $C_{STR}$ comprises a charged amino acid residue.

32. The adsorptive insoluble surface (IS) according to claim 3, wherein the at least one charged group $C_{SAR}$ has a negative charge.

33. The adsorptive insoluble surface (IS) according to claim 3, wherein the at least one charged group $C_{SAR}$ has a positive charge.

34. The adsorptive insoluble surface (IS) according to claim 3, wherein each charged group $C_{SAR}$ comprises a charged amino acid residue.

35. The adsorptive insoluble surface (IS) according to claim 1, wherein the charged groups enhance binding of a target which is net positive under binding conditions.

36. The adsorptive insoluble surface (IS) according to claim 1, wherein each ligand ADR joining region (AJR) comprises at least three of said charged groups ($C_{AJR}$) and wherein the at least three charged groups increase alpha-helicity-based stability.

37. A method of isolating at least one substance from a liquid comprising the steps of:

a) contacting the liquid comprising the at least one substance with the adsorptive insoluble surface (IS) according to claim 1, under conditions where each ligand affinity domain region (ADR) has the ability of binding the at least one substance, b) optionally washing the adsorptive surface, and c) eluting the at least one substance under conditions where each ligand affinity domain region (ADR) has reduced ability of binding the at least one substance.

38. A nucleic acid encoding a recombinant protein, said protein comprising n ligand affinity domain regions (ADR), wherein n is at least two, wherein each ligand affinity domain region (ADR) comprises a binding region of a protein selected from the group consisting of protein A, protein G, protein A/G, and protein L and derivatives thereof, and has the ability of specific binding of at least one substance, wherein one first ligand affinity domain region (ADR 1) is capable of binding to an insoluble surface (IS) with a surface attachment region (SAR) and wherein each ligand affinity domain region is bound to an adjacent ligand affinity domain region with a ligand ADR joining region (AJR), wherein each ligand ADR joining region (AJR) comprises at least three charged groups ($C_{AJR}$) between adjacent ADRs, wherein each charged group $C_{AJR}$ comprises a charged amino acid residue selected from glutamic acid and aspartic acid, and wherein the charged groups modify a net charge of the ligand in the absence of the charged groups.

39. The nucleic acid encoding a recombinant protein according to claim 38, wherein the n ligand affinity domain region (ADR) comprises a ligand solution terminal region (STR) comprising at least one charged group ($C_{STR}$).

40. The nucleic acid encoding a recombinant protein according to claim 38, wherein the surface attachment region (SAR) comprises at least one charged group ($C_{SAR}$).

41. The nucleic acid encoding a recombinant protein according to claim 38, wherein the number n of ligand affinity domain regions (ADR) is from 2 to 10.

42. The nucleic acid encoding a recombinant protein according to claim 38, wherein each ligand ADR joining region (AJR) comprises 3-10 charged groups $C_{AJR}$.

43. The nucleic acid encoding a recombinant protein according to claim 38, wherein each ligand ADR joining region (AJR) comprises 3-7 charged groups $C_{AJR}$.

44. The nucleic acid encoding a recombinant protein according to claim 38, wherein each ligand ADR joining region (AJR) comprises at least 5 charged groups $C_{AJR}$.

45. A protein expression system comprising the nucleic acid according to claim 38.

46. A method of manufacturing an adsorptive insoluble surface (IS) according to claim 1, comprising binding the ligand to the surface using a surface attachment region (SAR).

47. The method according to claim 46, wherein the ligand is a protein expressed in a protein expression system comprising a nucleic acid encoding a recombinant protein, said protein comprising n ligand affinity domain regions (ADR), wherein n is at least two, wherein each ligand affinity domain region (ADR) comprises a binding region of a protein selected from the group consisting of protein A, protein G, protein A/G, protein L, and derivatives thereof, and has the ability of specific binding of at least one of the at least one substance, wherein one first ligand affinity domain region (ADR 1) is capable of binding to the insoluble surface (IS) with a surface attachment region (SAR) and wherein each ligand affinity domain region is bound to an adjacent ligand affinity domain region with a ligand ADR joining region (AJR), wherein each ligand ADR joining region (AJR) comprises at least three charged groups ($C_{AJR}$) added between adjacent ADRs, wherein each charged group $C_{AJR}$ comprises a charged amino acid residue selected from glutamic acid and aspartic acid, and wherein the charged groups modify a net charge the ligand would have in the absence of the added charged groups.

* * * * *

SEQUENCE LISTING

<160> NUMBER OF SEQ ID NOS: 3

<210> SEQ ID NO 1
<211> LENGTH: 58
<212> TYPE: PRT
<213> ORGANISM: Mouse
<220> FEATURE:
<223> OTHER INFORMATION: Z sequence for Example 1
<300> PUBLICATION INFORMATION:
<301> AUTHORS: Feifan Yu, Peter Järver, Per-Åke Nygren
<302> TITLE: Tailor-Making a Protein A-Derived Domain for Efficient Site-Specific Photocoupling to Fc of Mouse IgG(1)
<303> JOURNAL: PLoS ONE
<304> VOLUME: 8
<305> ISSUE: 2
<306> PAGES: e56597
<312> PUBLICATION DATE: February 12, 2013

<400> SEQUENCE: 1

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 2
<211> LENGTH: 265
<212> TYPE: PRT
<213> ORGANISM: Escherichia coli

<400> SEQUENCE: 2

```
Met Gly Ser Ser His His His His His His Ser Ser Gly Leu Val Pro
1               5                   10                  15

Arg Gly Ser His Met Val Asp Asn Lys Phe Asn Lys Glu Gln Gln Asn
            20                  25                  30

Ala Phe Tyr Glu Ile Leu His Leu Pro Asn Leu Asn Glu Glu Gln Arg
        35                  40                  45

Asn Ala Phe Ile Gln Ser Leu Lys Asp Asp Pro Ser Gln Ser Ala Asn
    50                  55                  60

Leu Leu Ala Glu Ala Lys Lys Leu Asn Asp Ala Gln Ala Pro Lys Gly
65                  70                  75                  80

Ser Ser Val Asp Asn Lys Phe Asn Lys Glu Gln Gln Asn Ala Phe Tyr
            85                  90                  95

Glu Ile Leu His Leu Pro Asn Leu Asn Glu Glu Gln Arg Asn Ala Phe
            100                 105                 110

Ile Gln Ser Leu Lys Asp Asp Pro Ser Gln Ser Ala Asn Leu Leu Ala
        115                 120                 125

Glu Ala Lys Lys Leu Asn Asp Ala Gln Ala Pro Lys Ser Gly Gly Val
    130                 135                 140

Asp Asn Lys Phe Asn Lys Glu Gln Gln Asn Ala Phe Tyr Glu Ile Leu
145                 150                 155                 160

His Leu Pro Asn Leu Asn Glu Glu Gln Arg Asn Ala Phe Ile Gln Ser
            165                 170                 175

Leu Lys Asp Asp Pro Ser Gln Ser Ala Asn Leu Leu Ala Glu Ala Lys
        180                 185                 190

Lys Leu Asn Asp Ala Gln Ala Pro Lys Gly Ser Ser Val Asp Asn Lys
    195                 200                 205
```

```
Phe Asn Lys Glu Gln Gln Asn Ala Phe Tyr Glu Ile Leu His Leu Pro
    210                 215                 220

Asn Leu Asn Glu Glu Gln Arg Asn Ala Phe Ile Gln Ser Leu Lys Asp
225                 230                 235                 240

Asp Pro Ser Gln Ser Ala Asn Leu Leu Ala Glu Ala Lys Lys Leu Asn
                245                 250                 255

Asp Ala Gln Ala Pro Lys Ser Gly Gly
            260                 265

<210> SEQ ID NO 3
<211> LENGTH: 265
<212> TYPE: PRT
<213> ORGANISM: Escherichia coli

<400> SEQUENCE: 3

Met Gly Ser Ser His His His His His His Ser Ser Gly Leu Val Pro
1               5                   10                  15

Arg Gly Ser His Met Val Asp Asn Lys Phe Asn Lys Glu Gln Gln Asn
            20                  25                  30

Ala Phe Tyr Glu Ile Leu His Leu Pro Asn Leu Asn Glu Glu Gln Arg
        35                  40                  45

Asn Ala Phe Ile Gln Ser Leu Lys Asp Asp Pro Ser Gln Ser Ala Asn
    50                  55                  60

Leu Leu Ala Glu Ala Lys Lys Leu Asn Asp Ala Gln Ala Pro Lys Asp
65                  70                  75                  80

Asp Asp Val Asp Asn Lys Phe Asn Lys Glu Gln Gln Asn Ala Phe Tyr
                85                  90                  95

Glu Ile Leu His Leu Pro Asn Leu Asn Glu Glu Gln Arg Asn Ala Phe
            100                 105                 110

Ile Gln Ser Leu Lys Asp Asp Pro Ser Gln Ser Ala Asn Leu Leu Ala
        115                 120                 125

Glu Ala Lys Lys Leu Asn Asp Ala Gln Ala Pro Lys Asp Asp Asp Val
    130                 135                 140

Asp Asn Lys Phe Asn Lys Glu Gln Gln Asn Ala Phe Tyr Glu Ile Leu
145                 150                 155                 160

His Leu Pro Asn Leu Asn Glu Glu Gln Arg Asn Ala Phe Ile Gln Ser
                165                 170                 175

Leu Lys Asp Asp Pro Ser Gln Ser Ala Asn Leu Leu Ala Glu Ala Lys
            180                 185                 190

Lys Leu Asn Asp Ala Gln Ala Pro Lys Asp Asp Asp Val Asp Asn Lys
        195                 200                 205

Phe Asn Lys Glu Gln Gln Asn Ala Phe Tyr Glu Ile Leu His Leu Pro
    210                 215                 220

Asn Leu Asn Glu Glu Gln Arg Asn Ala Phe Ile Gln Ser Leu Lys Asp
225                 230                 235                 240

Asp Pro Ser Gln Ser Ala Asn Leu Leu Ala Glu Ala Lys Lys Leu Asn
                245                 250                 255

Asp Ala Gln Ala Pro Lys Asp Asp
            260                 265
```